United States Patent [19]

Vick et al.

[11] Patent Number: 5,473,942
[45] Date of Patent: Dec. 12, 1995

[54] ACOUSTIC LOCATION FIXING INSECT DETECTOR

[76] Inventors: Kenneth W. Vick, 104 E. Franklin Ave., Glen Dale, Md. 20769; Carl A. Litzkow, 18828 SW. 13th Ave., Newberry, Fla. 32669; Dennis Shuman, 4336 NW. 27th Dr., Gainesville, Fla. 32605

[21] Appl. No.: 963,171
[22] Filed: Oct. 19, 1992
[51] Int. Cl.$^6$ ................................................. G01N 29/14
[52] U.S. Cl. .......................... 73/587; 367/136; 367/180
[58] Field of Search .......................... 73/587, 591, 584, 73/602; 367/136, 139, 180; 340/540, 573

[56] References Cited

U.S. PATENT DOCUMENTS

| | | | |
|---|---|---|---|
| 4,592,034 | 5/1986 | Sachse et al. | 367/127 |
| 4,671,114 | 9/1987 | Litzkow et al. | 73/587 |
| 4,809,554 | 3/1989 | Shade et al. | 73/587 |
| 4,937,555 | 6/1990 | Litzkow et al. | 340/540 |
| 4,941,356 | 7/1990 | Pallaska | 73/587 |
| 4,991,439 | 2/1991 | Betts | 73/587 |

OTHER PUBLICATIONS

Milner et al, 1950, "Application of X-ray Techniques to the Detection of Internal Insect Infestation of Grain", J. of Econ. Entomol. v. 43:933.
Bruce et al, 1982, "Detection of Hidden Insect Infestations in Wheat by Infrared Carbon Dioxide Gas Analysis", Advanced in AGric. Tech., South Series, No. 26, USDA, 1–8.
Brian, 1924, "Preliminary Note on the Adaption of Certain Radio Principles to Insect Investigation Work", Ann. Univ. Stellenbosch, vol. 2, 45–47.
Adams et al, 1953, "Aural Detection of Grain Infestation Internally with Insects", Science, v. 118, 163–164.
Bailey et al, 1965, "The Detection of Immature Stages of Insects within Grains of Wheat", J. Stored Prod. Res., vol. 1, 201–212.
Street, 1971, "A Method for Aural Monitoring of In–Kernal Insect Activity", J. Ga. Entomol. Soc., v. 6, 72–75.
Webb et al, 1988, "Computerized Acoustical Larval Detection System", Appl. Eng. Agric., vol. 4, 268–274.
Vick et al, 1988, "Sound Detection of Stored–Product Insects That Feed Inside Kernels of GRain", J. Econ. Entomol, vol. 81, 1489–1493.
Hagstrum et al, 1988, "Acoustical Detection and Estimation of *Rhyzopertha Dominica* (F.) Larval Populations in Stored Wheat", Florida Entomol., v. 71, 441–447.
Hagstrum et al, 1991, "Automated Acoustical Monitoring of *Tribolium castaneum* (*Coleoptera: Tenebrionidae*) Populations in Stored Wheat", J. of Econ Entom., v. 84(5), 1604–1608.
Hagstrum et al, 1990, "Acoustical Monitoring of *Rhyzopertha Dominica* (F.) Larval Populations in Stored Wheat", J. Econ Entom., v. 83(2), 625–628.
Storey et al, 1982, "Insect Infestations in Wheat and Corn Exported from the United States", J. Econ. Entom. v. 75, 827–832.
Shuman et al, 1988, "Dual Roles of Visual Feedback on Postural STability", Trends in Ergonomics/Human Factors V, 169–176.
Spiesberger et al, 1990, "Passive Localization of Calling Animals and Sensing of Their Acoustic Enrironment Using Acoustic Tomography", The American Naturalist, v 135(1), 107–153.

*Primary Examiner*—Hezron E. Williams
*Assistant Examiner*—Rose M. Finley
*Attorney, Agent, or Firm*—H. Silverstein; J. Fado; Gail E. Poulos

[57] ABSTRACT

A device and a method for locating and counting insects in agricultural commodities has been developed. Acoustic sensors pick up sounds emanating from adult and or larval insects. The electrical outputs of the sensors are amplified and analyzed to determine (1) the first sensor to detect the sound, (2) the second sensor to detect the sound and (3) the time difference between the first and second detection. These determinations are used to calculate the locations and numbers of insects in the agricultural commodity samples.

17 Claims, 9 Drawing Sheets

ACOUSTIC LOCATION FIXING INSECT DETECTOR

BACKGROUND OF THE INVENTION

1. Field of the Invention

This invention relates to an apparatus and process for accurate quantitative determination by acoustical methods of insects present in agricultural commodities such as grains, fruits, nuts, vegetables, and legumes.

2. Description of the Prior Art

All grain being exported from this country, as well as most grain being bought for domestic human consumption, is inspected for insect infestation. Presently, inspection of grain is done by counting insects sieved from a defined sample, usually a 1 Kg. sample. This procedure limits detection to externally-feeding larvae and adults. Internally feeding larvae in grain are not detectable by usual methods of analysis, and if adult insects have been removed by cleaning of the grain, infested grain may be declared to be insect free. When these insects emerge days or weeks later, often after the grain has been moved, problems arise that are both legal (where and when did the grain become infested and who is financially responsible) and entomological (movement of insects from this infested grain to nearby uninfected grain creates an insect control problem). Also, larvae in grain kernels are a major source of insect fragments in milled products such as flour which create regulatory and public relations problems for milling companies.

Insects having internally feeding larvae include the lesser grain borer, *Rhyzopertha dominica* (F.), the rice weevil, *Sitophilus oryza* (L.), and the Angoumois grain moth, *Sitotroga cerealella* (Olivier). The eggs of these species are laid either on or in the kernels. Upon hatching, the larvae bore into the kernel and they emerge a few weeks later as adult insects after eating the contents of the grain kernel.

Various approaches to detect larvae in grain have been tried including X-ray analysis of grain (Milner, M., M. R. Lee and R. Katz. [1950]. J. Econ. Entomol. 43: 933–935) and detection of the $CO_2$ released by respiring insects (Bruce, W. A., M. W. Street, R. C. Semper, and David Fulk, [1982]. Advances in Agric. Tech., South. Series, No. 26, U.S. Dept. Agric. 1–8). These methods are costly, time consuming and generally not implemented. Detection of sounds produced by feeding larvae (Brain, C. K. [1924] Ann. Univ. Stellenbosch. 2: 45–47., Adams R. E., J. E. Wolfe, M. Milner, and J. A. Shellenberger [1953]. Science 118: 163–164, Bailey, S. W., and J. B. McCabe [1965]. J. Stored Prod. Res. 1: 201–212, and Street, M. W. [1971] J. Ga. Entomol. Soc. 6: 72–75) has also been tried but technical difficulties prevented the development of practical systems by later workers. Recent improvements in the sensitivity of acoustical systems for detecting insect larvae in grain suggest that this approach has considerable promise as a fast, simple and an inexpensive method for the practical problems of insect detection (Webb, J. C., C. A. Litzkow, and D. C. Slaughter, [1988]. Appl. Eng. Agric. 4: 268–274, Vick, K. W., J. C. Webb, B. A. Weaver and C. A. Litzkow [1988]. J. Econ. Entomol. 81: 1489–1493, Hagstrum, D. W., J. C. Webb, and K. W. Vick. [1988]Florida Entomol. 71: 441–447, U.S. Pat. Nos. 4,671,114 and 4,937,555).

However, these methods are effective only when the detection problem is simply a yes/no question—are insects present or not, such as in quarantine situations. The situation in grain is complicated by the presence of allowable infestation levels. Only if infestation levels rise above these threshold levels, are penalties accessed. Thus the detection of insects in grain is not a yes/no question, but a quantitative question of whether or not allowable threshold levels are exceeded. How many insects are present? The answer to this question is substantially more difficult to obtain than a yes/no answer, especially at the required accuracy levels. Both Vick et al. (1988), supra and Hagstrum et al. (1988) supra, demonstrated that the number of insect-produced sounds detected in a grain sample or in a grain bin with a grain probe is proportional to the number of insects in the sample or near the grain probe. Calibration curves can thus be produced by experimentally infesting grain at various infestation levels and counting the number of voltage spikes produced by the feeding sounds. Regression lines can be drawn correlating infestation levels to voltage spikes counted so that the numbers of insects in grain samples can be estimated by these voltage spikes. Unfortunately, the number of sounds detected in a grain sample (or with a grain probe in a grain bin) is also affected by the distance of the insect from the detector and the age of the larvae. Grain attenuates the sounds produced by feeding larvae such that an acoustic transducer will detect many more sounds from a larva near the transducer than from one located farther away. For a distant larva, only the strongest sounds are detected, whereas for a larva in close proximity to the transducer, the strongest sounds as well as much weaker sounds are heard. Errors of as much as 100 fold could be made in estimating infestation levels because of the distance effect on sound detection. To circumvent this source of error, grain samples would have to be acoustically analyzed several times with mixing of the sample between analyses in order to achieve an "average" number of sounds detected. The experiments used to collect the data for the calibration curves would have to be collected the same way to avoid introducing "distance" bias into the calibration curves.

Another unwanted correlate to number of sounds detected by the acoustic system is the age of the larvae. As shown by Vick et al. (1988) supra, young larvae produce fewer detectable sounds than older larvae. An extremely large population of very young larvae might produce few detectable sounds and would be mistaken for a small infestation. In most cases the larval population can be assumed to be a randomly mixed age and if the insects used to make the calibration curves were similarly of mixed ages, the error associated with age might largely be canceled out. There are cases where the larval population will not be of uniformly mixed age and in fact can be synchronized. This can happen at the start of a storage season or after a fumigation, for example. In cases of synchronized populations, very large errors can be inadvertently made, both over and underestimating the size of the larval population. Workers estimating larval populations by comparing total insect sounds detected in an unknown sample of grain to a calibration curve would have to be aware of the storage history for each sample that might have synchronized the larval population.

There is a need for a rapid, quantitative, and economic method for detecting larvae of major insect pests of agricultural commodities. The invention described below largely eliminates the problems associated with distance and larval age from the quantitation of population levels in stored agricultural commodities by acoustic means. It also allows the acoustical determination of the number of insects in a sample of grain, fruits, nuts, vegetables or legumes without the need for reference calibration curves.

SUMMARY

In accordance with the invention, insects, both adult and larval, infecting agricultural commodities are located and/or counted.

The apparatus of the invention, known as ALFID, (Acoustic Location Fixing Insect Detector), comprises:

(a) a container for holding agricultural commodities;

(b) a plurality of acoustic sensors acoustically attached to said container for detecting sound waves emanating from insects in said agricultural commodities and converting said sound waves to electrical signals;

(c) an amplifier means connected to each of said plurality of acoustic sensors for amplifying said electrical signals;

(d) an analyzer means connected to the said amplifier means for receiving the resulting amplified electrical signals and determining which of said plurality of acoustic sensors detects a sound emanating from an insect first, first detection, determining which of said plurality of acoustic sensors detects said sound second, second detection and determining the time interval between said first detection and said second detection; and (e) an indicating means connected to said analyzer means for using the determination made by said analyzer means to indicate presence and locus of possible points defining a plane which contains said insect, counting the total number of different planes, and equating the number of different planes to the number of different insects.

The present method of acoustical location fixing comprises the steps of (a) acoustically detecting sound waves emanating from insects in an agricultural commodity sample with a plurality of acoustical sensors and converting said sound waves to electrical signals;

(b) determining which of said plurality of acoustic sensors is first to detect sound waves emanating from an insect, first detection and which of said plurality of acoustic sensors is second to detect sound waves emanating from said insect, second detection;

(c) determining the difference in time between said first detection and said second detection;

(d) analyzing the determinations from step (b) and step (c) to determine a locus of possible points defining a plane which contains the detected insect;

(e) repeating steps (a) through (d) for each sound produced in said agricultural commodity samples;

(f) counting the total number of different planes determined by steps (a) through (e);

(g) equating the number of different planes to the number of different insects.

In accordance with this discovery it is an object of this invention to provide a quick, easy, and accurate quantitative determination of insects, particularly the number of larvae, infecting agricultural commodities.

Other objects and advantages of the invention will be readily apparent from the ensuing description.

BRIEF DESCRIPTION OF THE DRAWINGS

FIG. 1a uses a threshold detection means for analyzing which acoustic sensor detects sound waves first and second and determining the time difference between the two while FIG. 1b uses a cross-correlation method for the analyzing step. Only two sensors are shown for simplification.

DETAILED DESCRIPTION OF THE INVENTION

It will be clear from the following description that this invention can easily be adapted to detect insect infestation in many agricultural commodities including fruits, nuts, vegetables, legumes, grains, and to other applications such as insect infestation of wood.

Figure 1A:
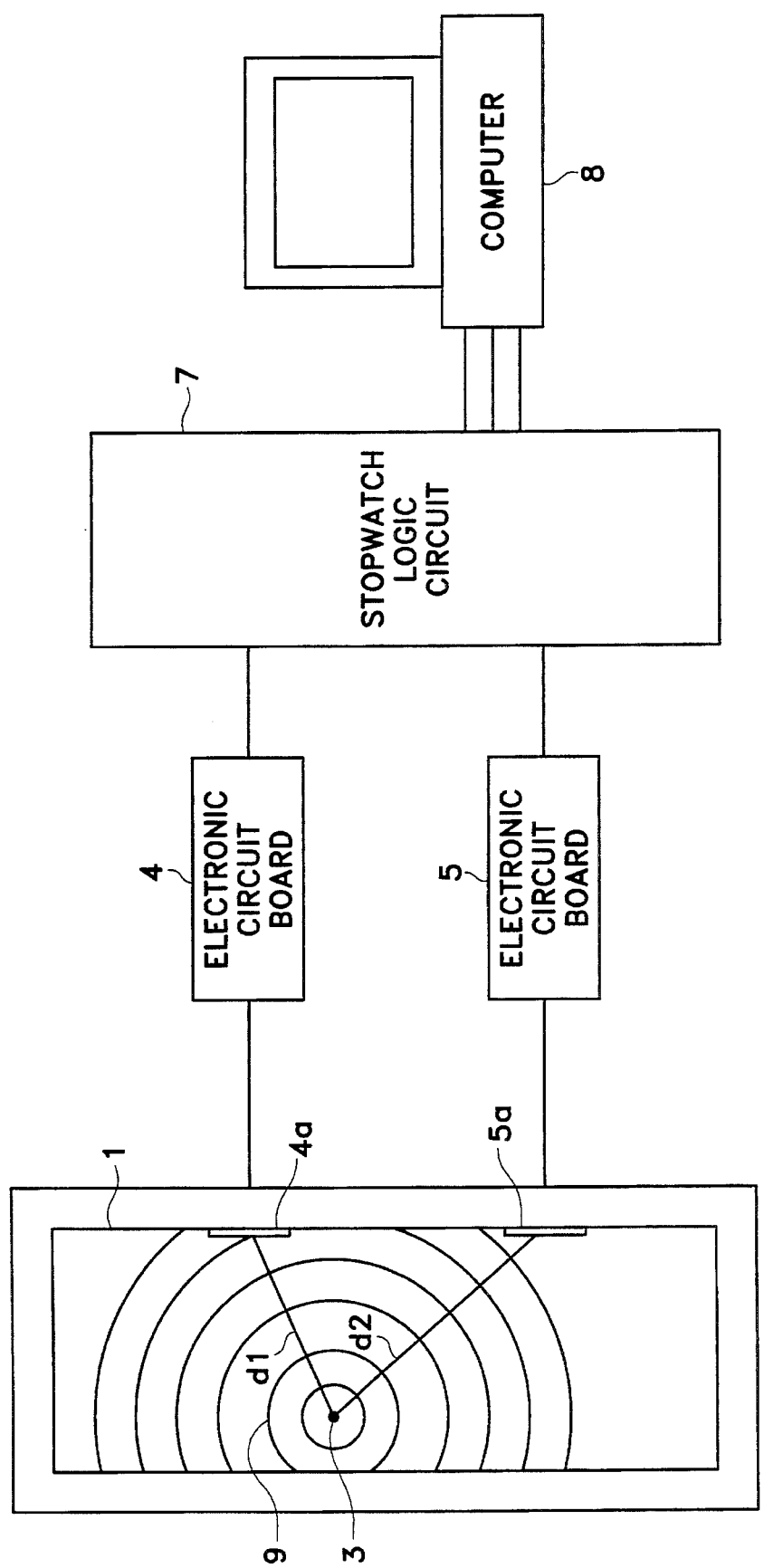
FIGS. 1a and 1b are a flow diagram of the basic components of the ALFID system.
Figure 1B:
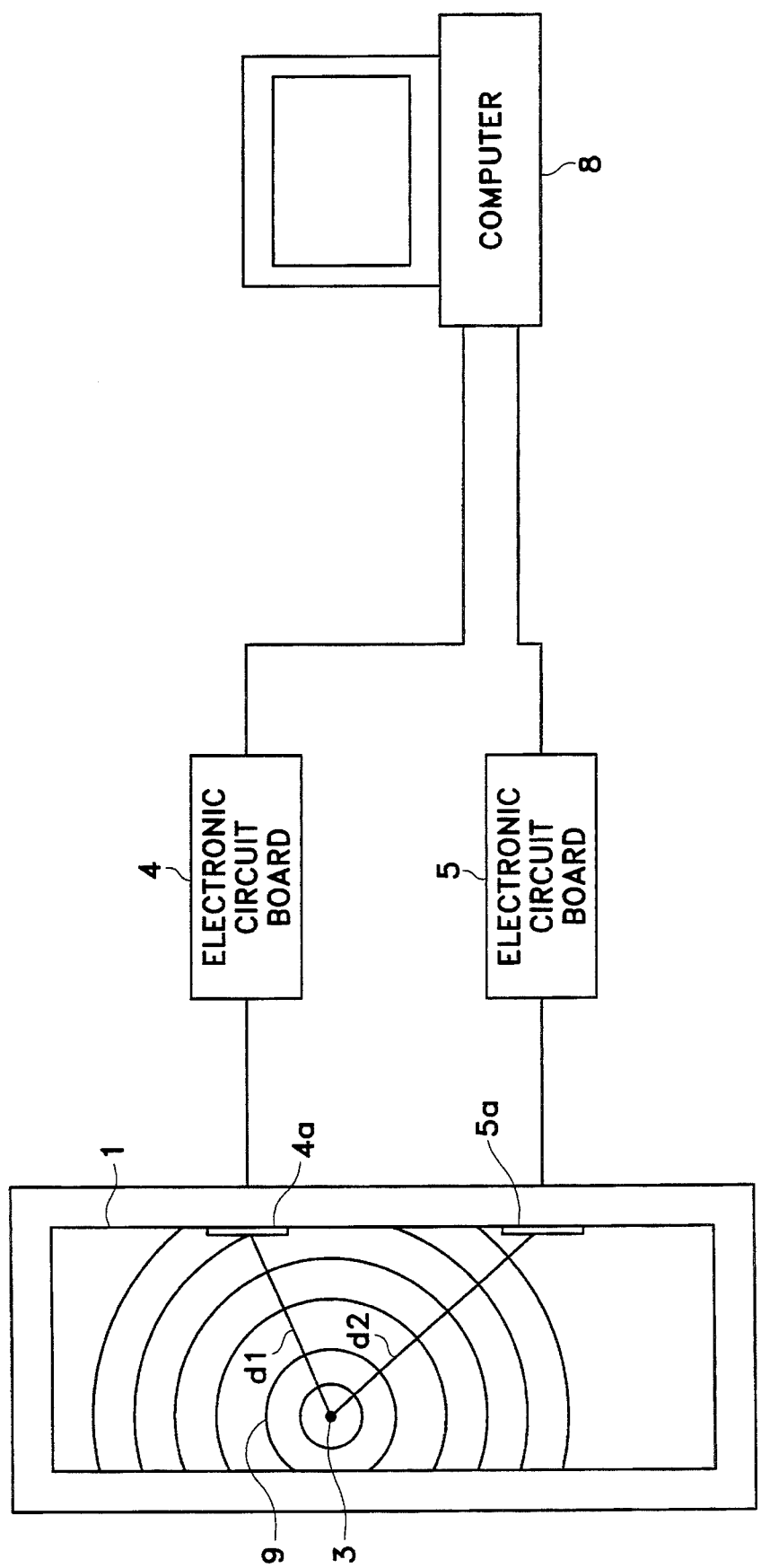

The invention uses a grain container 1 (FIG. 1a and 1b) in which grain samples are placed. The container can be made of any material, such as Lexan™, which is compatible with acoustic sensors 4a and 5a and is preferably of a size to hold about 1 Kg. of grain sample. The shape or dimensions of the container is important only in regard to the number and position of the transducers which can affect sensitivity. A container with a narrow cross-section is preferred. The container is preferably placed in a sound attenuation box to prevent ambient noise from reaching the sensors. An ambient noise detector which would disable data collection during the presence of excessive ambient noise, would provide additional protection from error due to ambient noise. The acoustic sensors, 4a and 5a (FIG. 1a and 1b) are attached to the grain container in a manner such that they can respond to sound within the container. Piezoelectric transducers which are sensitive to sound amplitude in a frequency range from 1–10 KHz are suitable. Sensors which have high sensitivity and flatness of response to frequencies of from 1.5 to 5.5 KHz also can be used. A linear array of sensors along a narrow side of the container is suitable. However, arrays on two or more sides would reduce the distance from the insect 3 to its closest sensor and increase sensitivity. This could also be accomplished by arrays mounted inside the container, which would provide the additional benefit of attenuation of ambient noise by the grain surrounding the sensors. Other types of transducer arrays and other shapes and sizes of the container will be obvious to those skilled in the art, especially when used with other agricultural commodities. When sound is emanating from an insect 3, it will occur more than once from the same location, the same sensors will detect the sound in the same order and the time interval will be the same. However, if the sound emanates from some other source (e.g. grain settling), it would usually occur only once from the same location. When the three parameters from multiple sounds are compared, insect and transient sounds can be differentiated.

One embodiment, an amplitude threshold hardware approach, has the advantages of lower cost and greater accuracy in situations where the acoustic signals are not distorted by a non-homogenous acoustic medium, by noise, and by non-uniformity and lack of flatness of the transducers' frequency responses. The output of each sensor is amplified and threshold detected before being sent to analyzer means 7 (FIG. 1a) which is a logic circuit. Preferably the sensor output is amplified by a high gain amplifier, bandpass filtered and detected by a threshold detector (all part of 5 in FIG. 1a) which gives a constant output level whenever the signal amplitude is greater than a predetermined threshold—i.e. the detector output is always at one of two possible levels or is digital in nature. This threshold is preferably set at a level slightly higher than the highest background noise.

The logic circuit has the sole purpose of specifying three parameters for each insect sound: (1) determining which sensor is first to detect a sound emanating from an insect, (2) determining which sensor is second to detect the same sound emanating from that insect, and (3) determining the time interval between the first detection and the second detection. These parameters collected from each sound occurring in the sample are sent to indicator 8 where they are stored until the end of the testing period. Indicator 8 counts the number of insects detected in this manner and displays the total. A PC type computer is suitable for use as indicator 8 and can be of further use in controlling the logic circuit using the ALFID software program in Appendix A.

In another embodiment, the hardware function amplifies and filters the sensor outputs, as above. However, the analyzing step is performed by a cross-correlation method which is a software intensive approach that involves digitizing and storing the raw signal waveforms, and then performing digital signal analysis to calculate the arrival time-difference. Since this method only responds to correlated signals, uncorrelated electronic noise is ignored and only correlated noise, such as low frequency power noise, needs to be filter by hardware. Thus, simple broadband filtering is adequate. Furthermore, this embodiment is useful when the acoustic signals are distorted by a non-homogenous acoustic medium, by noise, and by non-uniformity and lack of flatness of the transducers frequency responses.

A new function that is needed in this embodiment is the generation of a trigger signal. Insects produce sounds irregularly and most of the time they are quiet. In order to not fill large amounts of computer memory with background noise or 'dead space', a trigger signal is used to initiate each acquisition of a block of acoustic signal data. The timing of the trigger is not critical and can occur well into the acoustic signal while still insuring that the beginning of this signal is captured by using a pre-trigger operating mode. Therefore, triggering can be made to occur when an acoustic signal simply crosses a pre-assigned threshold value, and this value would also insure a minimum robustness of any acoustic signal that is captured. Since the identities of the pertinent sensors are unknown at the time of acoustic signal data acquisition, the amplified output waveforms of all sixteen sensors are collected when triggering occurs. Subsequent inspection of each block of collected data during the analysis phase reveals the identity of the sensor whose output caused the triggering to occur. Cross-correlations can then be performed between that output signal and adjacent sensors' output signals and even between those adjacent sensors' output signals and the output signals of the sensors adjacent to them (in case the triggering was not caused by one of the two sensors closest to the source of the sound), for a total of four cross-correlograms.

The following examples will further illustrate the invention.

EXAMPLE 1

Figure 3:
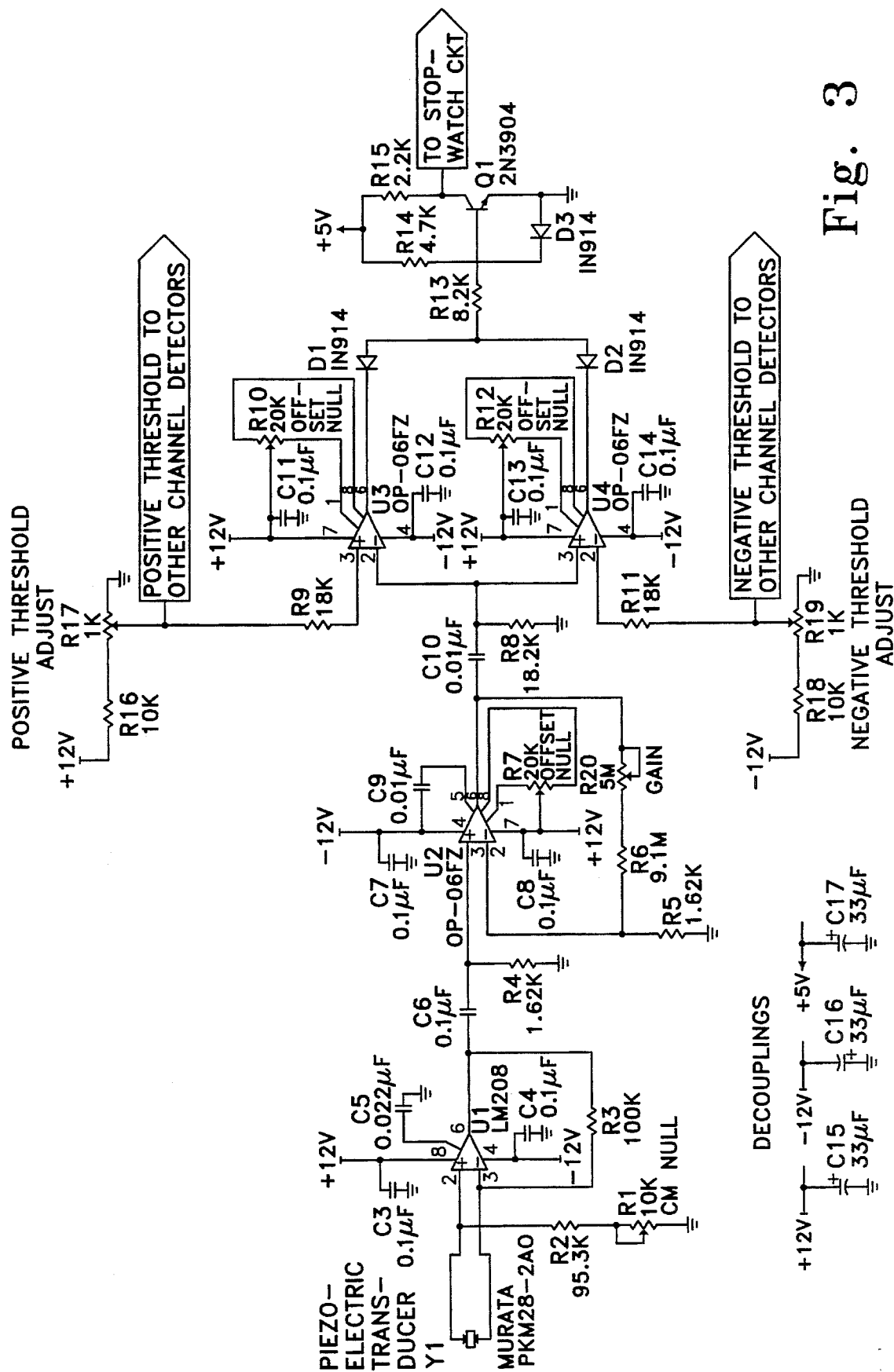
FIG. 3 is a schematic diagram of the Amplifier/Detector circuit.
Figure 4:
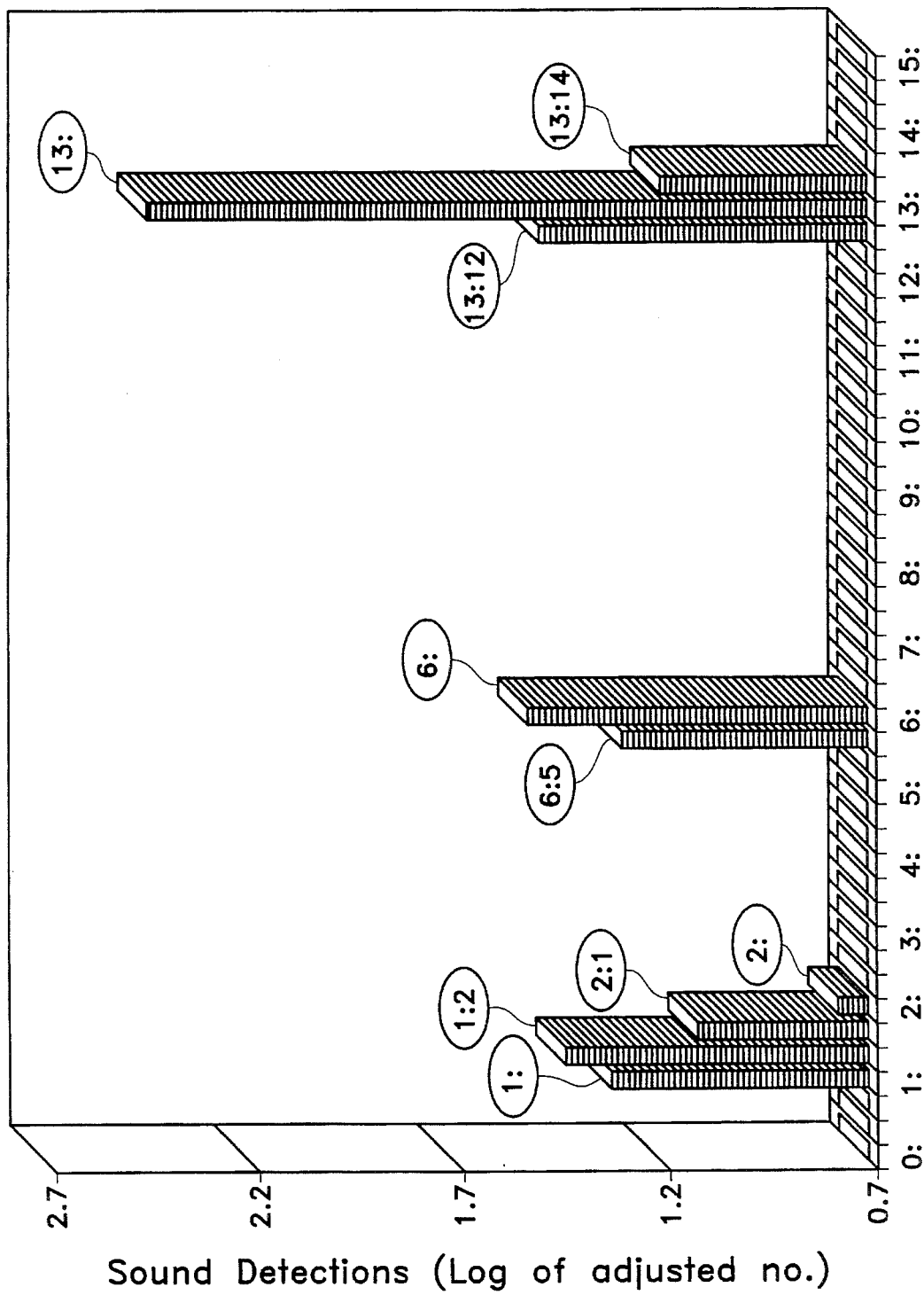
FIG. 4 is a graph of a representative trial when 3 insects were placed in the grain container.

This example of the ALFID system uses the amplitude threshold hardware approach. A 1 kg grain container 1 (76×5×4 cm) with a linear array of sixteen piezoelectric acoustic sensors 4a and 5a (spacing interval=4.8 cm) installed on one wall of the container is used. For field use, the container is oriented vertically to facilitate gravity loading and unloading of grain. A sixteen channel electronic circuit board 4 and 5, FIG. 3, positioned on an adjacent wall as close as possible to the sensors in order to reduce susceptibility to noise, locally amplifies and filters the low level sensor output and then threshold detects the signal.

The amplifier portion of the circuit is a two stage amplifier which incorporates bandpass filtering resulting in a frequency dependent gain function with a peak gain of 90 dB. The transducers are buffered by a differential amplifier utilizing a National Semiconductor LM 208A operational amplifier (U1). Any operational amplifier as known in the art which is capable of buffering the transducer may be used. The high input impedance op amp is heavily compensated (C5) for the desired high frequency roll off. The differential input amplifier configuration is incorporated to reduce common-mode power noise pick-up. Furthermore, a trimmer potentiometer (R1) is used to maximize common-mode rejection and thus minimize the noise. The output signal of this first stage is capacitively coupled (C6 and R4, to provide attenuation at low frequencies) to a high gain second stage. This second stage utilizes a PMI OP-06F high gain instrumentation operational amplifier (U2) in a non-inverting configuration and heavily compensated (C9) to again provide high frequency roll off. Again, any operational amplifier capable of providing a high gain may be used. A gain adjustment (R20) is incorporated to compensate for variations in transducer sensitivity and an offset null adjustment (R7) is incorporated to minimize the possibility of saturating the amplifier output. The output signal of this second stage is capacitively coupled (C10 and R8, to again provide attenuation at low frequencies) to the detector circuitry.

The detector portion of the circuit is a bipolar threshold detector. It utilizes two PMI OP-06F operational amplifiers (U3 and U4) as comparators to provide a low output if the input signal goes above a positive threshold (value adjusted by R17) or below a negative threshold (value adjusted by R19). Offset null adjustments are provided to improve the threshold level accuracy of the comparators. The comparator outputs are connected together through diodes (D1 and D2) to perform a logical OR function.

The detector output is interfaced to the logic circuit via a level convertor. NPN switching transistor (Q10) logically inverts the detector output and converts the signal voltages to standard Transistor-Transistor logic (TTL) compatible levels (0 volts and +5 volts). The level converters output to the stopwatch circuit is a logical "0" when there is no acoustic signal and a train of logical "1" pulses when a sufficiently large acoustic signal is present. A diode (D3) protects the transistor from large negative voltages on the detector output.

The complete unit was housed in an anechoic chamber to perform the function of the sound attenuation box. In the field a sound attenuation box is used. A cable from the digital output of the sixteen level convertors connected the unit to a remote (outside the chamber) logic circuit.

The logic circuit 7 (FIG. 1), named the stopwatch circuit, was connected to a commercial digital I/O and counter/timer board mounted inside an adjacent PC type computer 8 with at least a 12 Mhz clock.

The main functions of the stopwatch circuit are (1) to capture the identities of the amplifier channels that detect an incoming sound front 9 first and second, (2) to control the counting of a timer in order to ascertain the interval between these two detections, and (3) to initiate a hardware computer interrupt that allows the amplifier channel identities and the interval timer to be read and stored in the host computer. In performing this function, the stopwatch circuit also differentiates between ongoing and newly originating sounds. The circuit is an asynchronous digital circuit which allows it to respond virtually instantaneously (within nanoseconds) to changing inputs. It is composed of 28 standard low power Schottky TTL integrated circuit chips and a few passive components. Its inputs are from an array of amplifier/detectors and a digital I/O and counter/timer board which interfaces with the host computer. The stopwatch circuit's outputs are connected to the digital I/O and counter/timer board.

Figure 2:
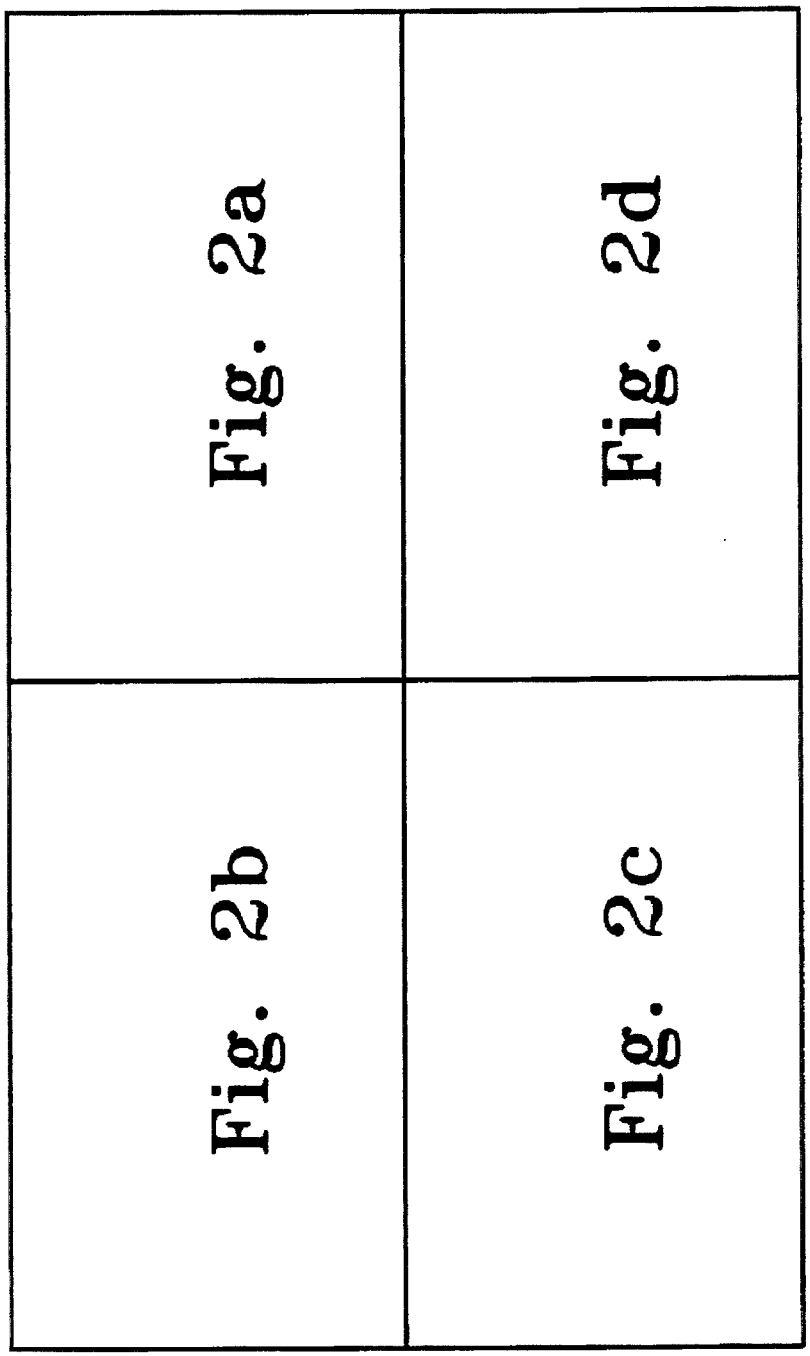
FIG. 2 is an illustration of the spatial relationship of FIGS. 2a–d.
Figure 2A:
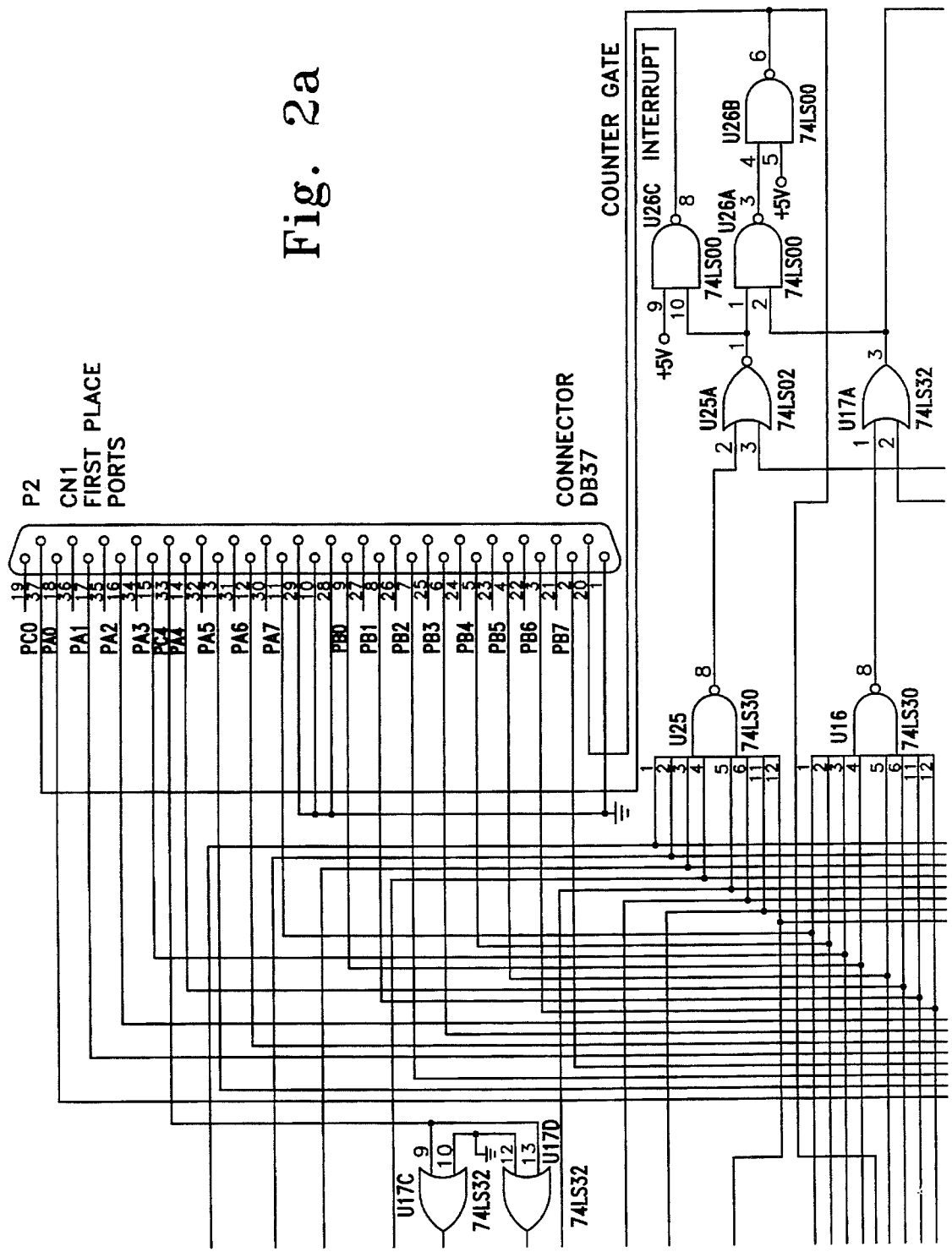
FIGS. 2a, b, c and d are a schematic diagram of the complete stopwatch circuit.
Figure 2B:
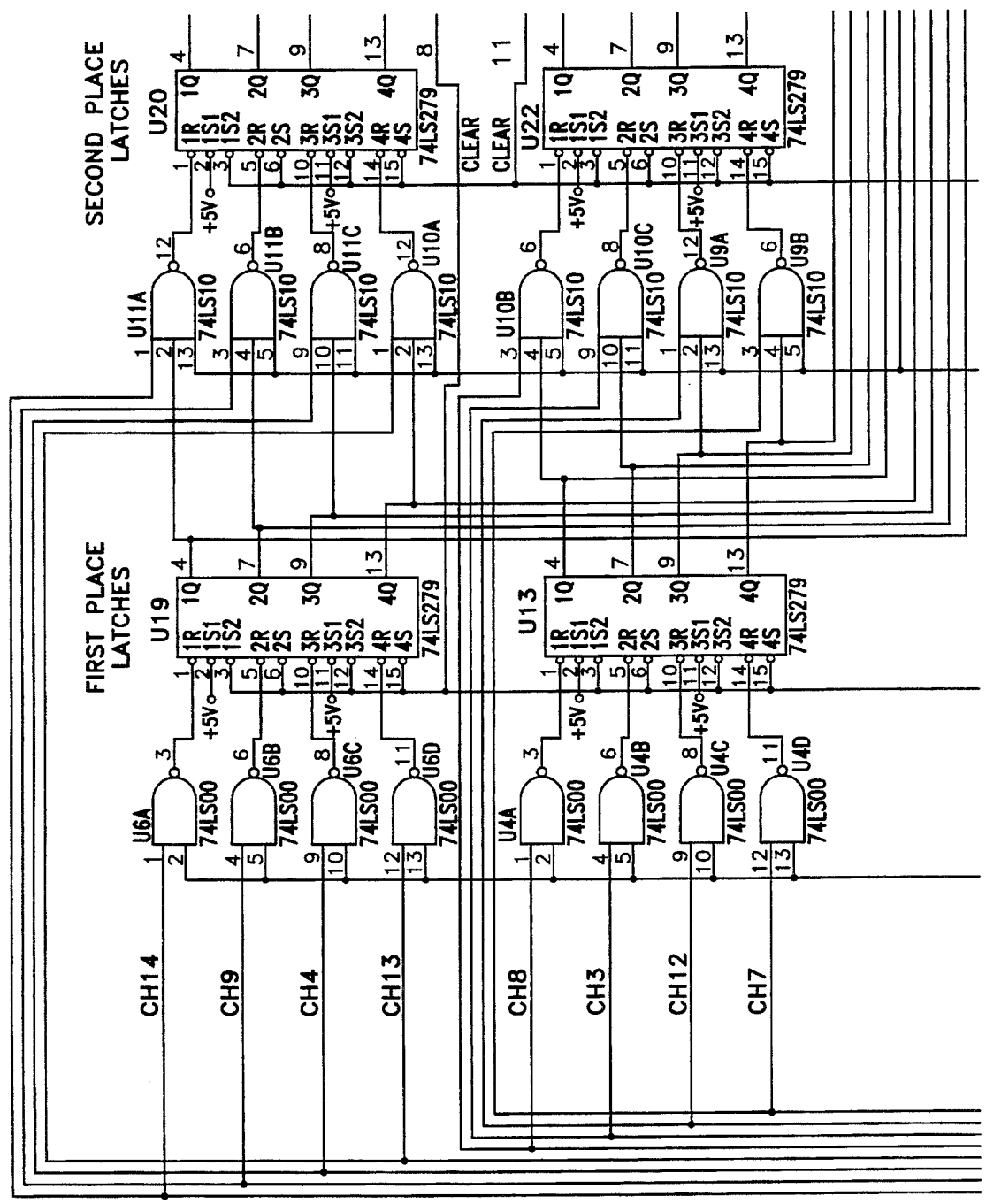
Figure 2C:
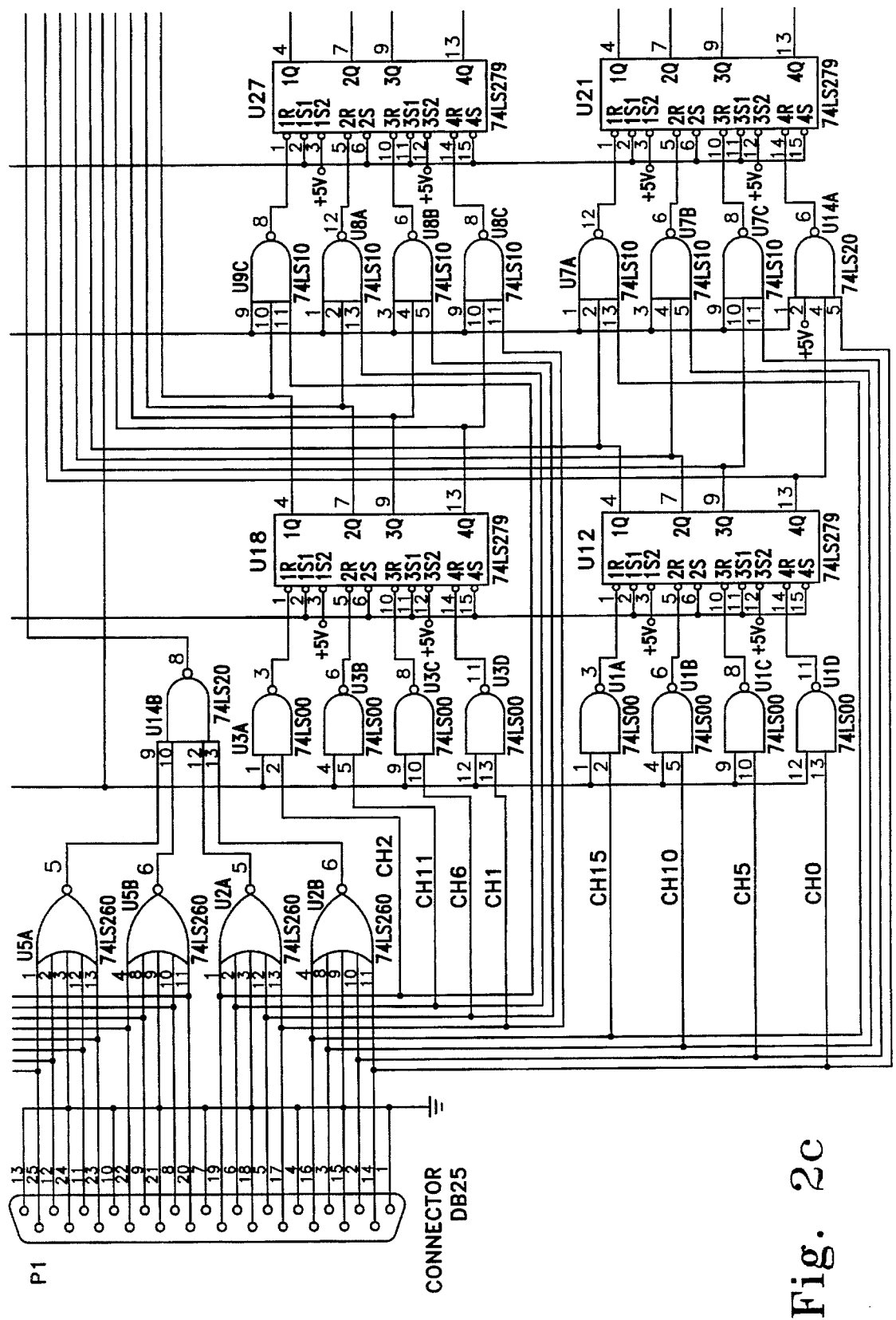
Figure 2D:
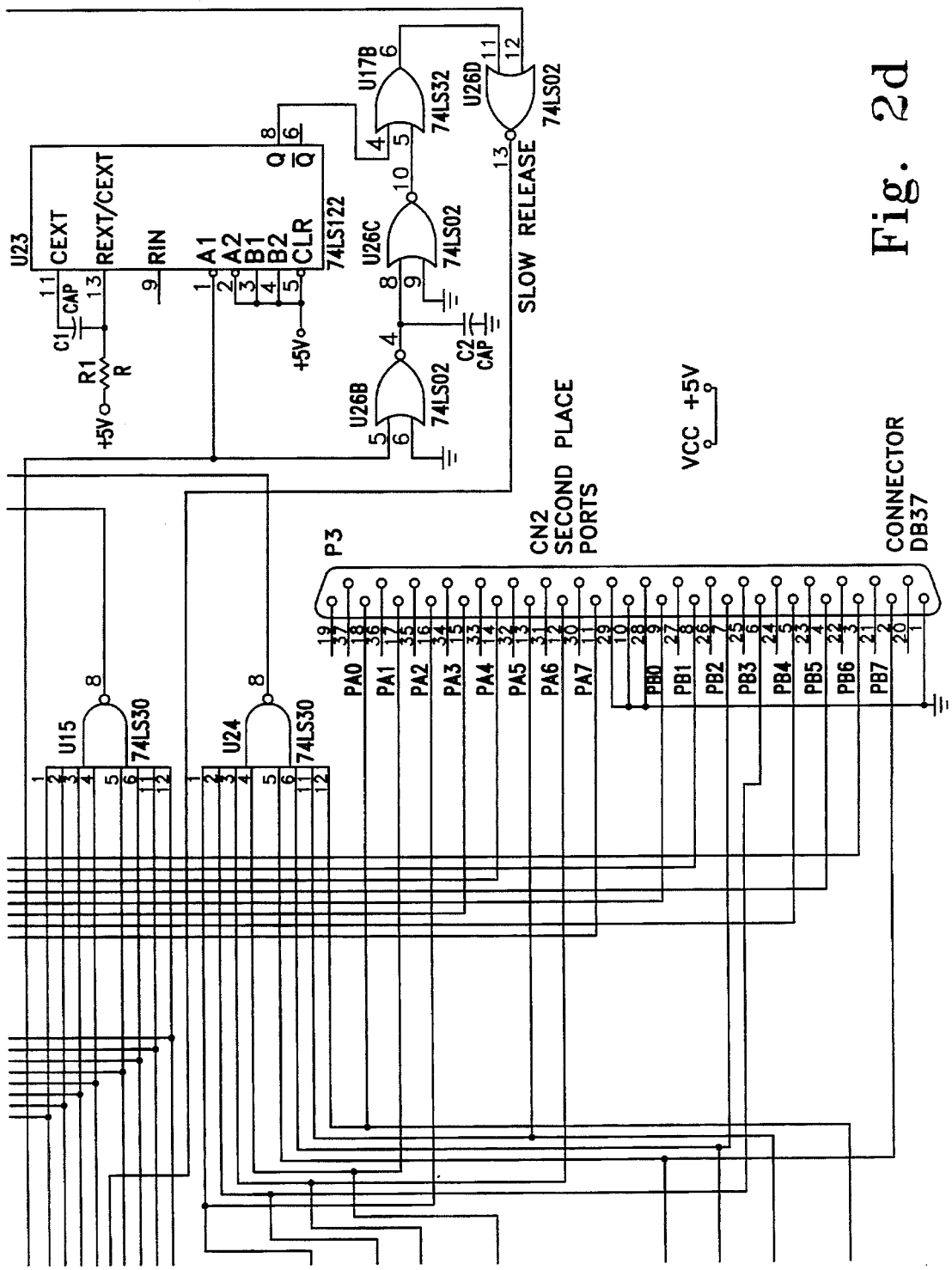

The stopwatch circuit schematic drawing is shown in FIG. 2. The 16 amplifier/detector channels' outputs are transmitted over a shielded ribbon cable and enter the circuit via the DB25 connector P1. The assignment of the channel numbers (0–15) on this cable was made in order to minimize crosstalk between adjacent channel numbers and thus reduce false acoustic source detection counts. False counts due to crosstalk between non-adjacent channel numbers can be easily eliminated by software analysis of the data. Table 1 summarizes the input/output pin numbering. With this arrangement adjacent channel numbers are separated by a minimum of three other lines, with at least one of them being a ground line.

The 16 channels' outputs are gated to corresponding arrays of 16 first place latches (U19, U13, U18, U12) via their enable gates (U6, U4, U3, U1) and 16 second place latches (U28, U22, U27, U21) via their enable gates (U11, U10, U9, U8, U7, U14A). Before circuit operation can begin, the circuit must be initialized by setting all the latches' outputs to "1"s. This is accomplished by the clear pulse generated by the computer, transmitted via connector P2 pin 33 (CN1 PC4 on the digital I/O board), and then buffered by drivers (U17C, U17D). In this initial state the first place latches are enabled (by the "1" output of U26B) and the second place latches are disabled (by the "0" output of U20B).

In the absence of an acoustical signal, the output of an amplifier/detector channel is a "0". When an acoustical signal is detected by a channel, its output appears as an irregular train of pulses that can persist from several msec to several seconds. The first pulse in the train resets its corresponding first place latch. It also disables the remaining first place latches by way of a channel summing network (U5, U2, U14B) which feeds an instant response slow release network (U23, U26B, U26C, U17B). This insures that only one first place latch can be reset. The slow release network incorporates a retriggerable one-shot (U23) triggered by the trailing edge of each train pulse to bridge the gaps between the pulses. The one-shot output pulse width (set by R1 and C1) is adjusted empirically to bridge the largest gaps encountered during a single insect sound. The output of the slow release network (U17B) therefore becomes a "1" at the beginning of the first pulse in the train and remains a "1" until the pulse train has been over for a period of time equal to the one-shot pulse width. There is a race condition in the slow release network caused by the input to output propagation delay of the one-shot (33 nsec max.) which causes a glitch in output when the train pulse ends and the one-shot is triggered. This condition is fixed by using two inverters (U26B, U26C) and inserting a delay capacitor (C2=680 pF) between them to bridge the glitch. There is also a first place latches summing network (U16, U15, U17A) whose output is added (via U26D) to the output of the slow release network to generate the first place latches enable. The final result is that the first place latches are disabled by the first pulse in a channel output pulse train and this disable persists as long as the channel output pulse train lasts or until the first place latches are cleared (by the host computer), which ever is longer.

When one of the first latches is reset by an incoming acoustical signal, besides disabling the remaining first place latches, the second place latches are enabled by the "1" output of the first place latches summing network (U17A) gated (via U20A, U20B) by the "1" output of a second place latches summing network (U25, U24, U26A). This second place latches enable signal ("1") is applied to all 16 second place latches' enable gates. However, each of these enable gates has an input from its corresponding first place latch so that the acoustical channel which resets the first place latch cannot reset the corresponding second place latch (i.e., the same channel cannot be both first and second).

The second place latches enable signal (U20B) is also the gate for the interval time counter on the digital I/O and counter/timer board via connector P2 pin 20 (GATE 2 on the digital I/O board). By becoming "1" when a first place latch is reset, it begins the timing of the interval between when a first place latch and when a second place latch is reset.

The next channel to detect an acoustical signal then presents a similar train of pulses as described before, the first of which resets its corresponding second place latch. This changes the output of the second place latches summing network (U26A) and then the second place latches enable signal (U20B) to "0". The remaining second place latches are thus disabled to insure that only one second place latch is reset. In addition this signal also stops the interval timer counter which now contains the desired information. The output of the second place latches summing network (U26A) is also inverted (U20C) to produce a "0" to "1" transition when a second place latch is reset. This transition is used to initiate a hardware interrupt of the host computer via connector P2 pin 37 (CN1 PC0 on the digital I/O board). The interrupt causes the computer to perform a routine which reads the latches (first place latches via connector P2 and second place latches via connector P3) and the interval timer counter and then clears them in preparation for the next operational cycle of the stopwatch circuit. It should be remembered, however, that the next cycle cannot begin until the previous channel output pulse train (coming in on any of the 16 channels because of the channel summing network) has been over for a period of time equal to the one-shot pulse width (due to the output of the slow release network).

The computer uses An ALFID software program, named ALFID18 and written in C, which mainly provides a driver to service the digital I/O board (containing 40 digital I/O lines and 3 counter/timers) that acts as an interface between the stopwatch circuit and the computer. It also organizes and summarizes the collected data and stores these results in several files. See Appendix A.

The program first initializes the computer and the digital I/O board in preparation for data collection. It queries the user about the desired test duration and data storage file names. The program then clears the stopwatch circuit latches and keeps track of elapsed test time. Whenever the stopwatch circuit initiates an interrupt, an interrupt service routine (ISR) a) reads the first and second place latches (via 32 of the digital I/O lines)/b) reads a counter/timer that was internally clocked and gated by the stopwatch circuit to act as the interval time counter, c) reads the computer's real time clock to time stamp the collected data, d) stores all this information in an array, e) resets the counter/timer, and f) clears the stopwatch circuit latches. This process continues until the program terminates when either the desired test duration has elapsed, the <Esc> key is pressed, or the data buffer is filled. Before termination, the data in the array is used to create 4 files that are stored on the computer's hard drive. One is used to display the raw data, one formats the raw data for analysis and the other two collapse and summarize the data for display and spreadsheet analysis. The data analysis could also be incorporated into the ALFID program so that the final output of the program would be the number of insects in the grain sample.

TABLE 1

Stopwatch Circuit Board Input/Output Pin Numbering

| Ribbon Cable 5 order | Channel number | Input pin DB25 | 1st Place Output CN1 DB37 | 2nd Place Output CN2 DB37 |
|---|---|---|---|---|
| 1 | gnd | 1 | * | * |
| 2 | 0 | 14 | PA0 18 | PA0 18 |
| 3 | 5 | 2 | PA5 13 | PA5 13 |
| 4 | gnd | 15 | * | * |
| 5 | 10 | 3 | PB2 7 | PB2 7 |
| 6 | 15 | 16 | PB7 2 | PB7 2 |
| 7 | gnd | 4 | * | * |
| 8 | 1 | 17 | PA1 17 | PA1 17 |
| 9 | 6 | 5 | PA6 12 | PA6 12 |
| 10 | gnd | 18 | * | * |
| 11 | 11 | 6 | PB3 6 | PB3 6 |
| 12 | 2 | 19 | PA2 16 | PA2 16 |
| 13 | gnd | 7 | * | * |
| 14 | 7 | 20 | PA7 11 | PA7 11 |
| 15 | 12 | 8 | PB4 5 | PB4 5 |
| 16 | gnd | 21 | * | * |
| 17 | 3 | 9 | PA3 15 | PA3 15 |
| 18 | 8 | 22 | PB0 9 | PB0 9 |
| 19 | gnd | 10 | * | * |
| 20 | 13 | 23 | PB5 4 | PB5 4 |
| 21 | 4 | 11 | PA4 14 | PA4 14 |
| 22 | gnd | 24 | * | * |
| 23 | 9 | 12 | PB1 8 | PB1 8 |
| 24 | 14 | 25 | PB6 3 | PB6 3 |
| 25 | gnd | 13 | * | * |

*gnd pins are 1, 10, 28, 29
Time gate input is CN1 pin 20
Interrupt input is CN1 PC0 pin 37
Clear output is CN1 PC4 pin 33

A 1 kg grain sample was poured into the container and the program was initiated after a few minutes to allow for grain settling. At the end of a specified time interval, the computer summarized the sensor identity data.

The rice weevil, Sitophilus oryzae (L.), was used as the test species in this study because larval stages feed exclusively within grain kernels and previous studies have shown that larvae produce sounds that are detectable by available piezoelectric sensors. Individual kernels were taken from cultures that were of such an age as to contain last instar larvae. One day prior to use, the presence of a larva within a kernel was determined by listening to individual kernels that were placed on a piezoelectric microphone. Controls (uninfected kernels) were obtained from samples that had been kept at −10° C. until about twenty-four hours before use. The ALFID system was evaluated by means of a double-blind test in which the number of kernels (infested and controls) and their locations within the grain sampling unit were identified by a first person who coded the information which was given to a second person who placed the kernels in the unit and ran the test. A third person analyzed the data that were recorded by the computer. The sampling unit was divided into sixty-three equally spaced deployment positions. These were along a line 3.3 cm above the centers of the sensors with horizontal deployment positions located directly above sensors, at ¼ sensor spacing intervals (11.9 mm) between sensors, and at a ¼ sensor spacing interval outside the two end sensors. The unit contained 1 kg of uninfected wheat which had been placed into the unit twenty-four hours prior to testing. In each trial, three kernels were placed in the unit at locations selected by a random number generator. Treatments (infested or uninfected kernels) were also selected at random for each trial.

A total of three hundred trials were conducted over a five week period with no more than twenty trials being conducted on a given day. Temperature was 26°±2° C. unless otherwise noted. After the placement of a treatment into the unit just below the grain surface, a one minute period was provided prior to testing to reduce background noise that resulted from operator movements of the unit. Each trial lasted nine minutes after preliminary tests showed that during this period any larvae present had a high likelihood of producing sounds. The detected sounds were then used to quantify infestation based on the following analysis:

1. The program reads the logic circuit for the location (sensor #) of the first and (possibly) second sensors to hear a given sound. For example, if a given sound was heard first by sensor 5, and then by sensors 4, it is assigned to a 5:4 Sensor Detection Order (SDO) by the ALFID software and is considered possible evidence of an insect located between sensors 4 and 5. If a sound is heard only by sensor 4, it is assigned to a 4: SDO and is considered possible evidence of an insect somewhere between sensors 3 and 5. If a sound is heard first and second by two non-adjacent sensors, it is considered an error, is not assigned to an SDO (e.g., there is no 4:6 SDO), and is not used in scoring. Thus, with sixteen sensors, there are forty-six possible SDOs that sounds could be assigned to and many sounds could be assigned to the same SDO. An SDO is not itself a position.

2. Subtraction of background noise. In thirty-three preliminary runs with no insects background noise resulted in small numbers of sounds being detected and assigned to various SDOs. 2 was subtracted from all test data for the sixteen possible SDOs involving one sensor and a value of 1 was subtracted from all test data for the 30 possible SDOs involving two sensors.

3. Ideally, all the sounds produced by a single insect would be assigned by the ALFID system to the same SDO. However, due to noise and non-uniform sound production and transmission, different sounds originating from activity of one insect could be assigned to different adjoining SDOs. For a number of sounds to be grouped together as having been produced by the presence of a single insect and thus considered a positive score, the algorithm used was:

a) if the sounds were assigned to only one SDO, then that SDO value (i.e., the number of sounds assigned to it) had to be greater than 7;

b) if the sounds were assigned to two adjoining SDOs (e.g. 4:5 and 5:4, or 4:5 and 4:), the both values had to be greater than 3;

c) if the sounds were assigned to three adjoining SDOs, then two of the three had to be greater than 2;

d) if the sounds were assigned to four adjoining SDOs, then at least two had to be greater than 2;

e) if the sounds were assigned to five adjoining SDOs, then at least one had to be greater than 1;

f) if the sounds were assigned to six or more adjoining SDOs, then each of them have to be greater than zero.

4. For graphic representation of the data, a value of 3 is added to each corrected SDO value (to obtain a positive integer, see 2 above) to allow plotting on a log scale. FIG.

4 shows an example of a representative trial when 3 insects were placed in the grain container.

Similar algorithms could be empirically established by one skilled in the art for different test conditions.

For statistical analysis, data from fifty consecutive trials were pooled and are considered to constitute one replication. Data from four trials were omitted as temperature fluctuations of greater than 10° C. occurred during these runs and adversely affected collected data. Mean and standard error values were calculated by routine methods. Examination of the data in terms of industry standards (0–1 insects/kg=clean grain, and greater than 1 insect/kg=infested grain) was accomplished by pooling data from trial with zero or one insect for the former, and trials with two or three insects present for the latter.

The results of the two hundred and ninety-six trials of the ALFID unit are summarized in Table 2. In about ninety percent of the trials in which no insects were present (N=34), the analysis was correct; about ten percent of these cases (N=3) were erroneously scored as having one insect present, and no trials were scored as having more than one insect present when, in fact, there were none. When one insect was present in a trial, it was correctly identified as such in about seventy percent (N=66) of the cases; such trials were incorrectly scored as having no insects present in about nineteen percent (N=19) of the trials; false positive (scored as two insects when only one was present) occurred in about eleven percent (N=10) cases; no trials were incorrectly scored

TABLE 2

ACCURACY OF IDENTIFICATION OF GRAIN INFESTED WITH *Sitophilus oryzae*

| Number of larvae present | Percent identified as: | | | |
|---|---|---|---|---|
| | N | 0 | 1 | 2 | 3 |
| 0 | 37 | 90.1 | 9.9 | 0.0 | 0.0 |
| 1 | 95 | 19.3 | 69.8 | 10.9 | 0.0 |
| 2 | 119 | 3.2 | 38.5 | 55.1 | 3.3 |
| 3 | 45 | 0.0 | 21.9 | 48.7 | 29.2 | as having three insects present when only one was present. When two insects were present, they were correctly identified in fifty-five percent (N=65) of the cases; the number present was underestimated about forty percent of the time (N=50), and overestimated in only three percent (N=4) of the cases. When three insects were in the unit, they were correctly assessed about twenty-nine percent (N=13) of the cases, and underestimated about seventy-one percent (N=32) of the time.

In summary, only six percent of the trials were incorrectly identified as having more insects present than were actually placed in the unit. The main cause of this error was high background signals which were incorrectly interpreted as larval presence. By far the greatest error (about thirty percent) was due to failure to identify larvae that were

TABLE 3

ACCURACY OF ALFID SYSTEM IN ASSESSING NUMBERS OF *SITOPHILUS ORYZAE* LARVAE IN GRAIN SAMPLES USING INDUSTRY STANDARDS

| Measurement | Clean Grain (0–1 Insect/kg) | Infested Grain (>1 Insect/kg) |
|---|---|---|
| N | 132 | 164 |
| % correct | 92.0 | 63.5 |
| SEM | 2.6 | 3.6 |
| 95% CL | 86.9–97.1 | 65.6–78.6 | present. This error was due to two different causes. First, when the randomization procedure for placing insect in the unit was performed, about fifteen percent of the cases yielded insect placements of less than 1.75 sensors apart, which was less than the limit of resolution of this embodiment. Secondly, some insects (about fifteen percent) did not make sounds that were above the threshold levels that had been set for noise reduction. The latter finding is perhaps related to the finding of Vick, et al, (1988) that *S. oryzae* produce sounds about ninety percent of the time during the larval stage.

Table 3 summarizes the results in terms of industry standards. Samples that contained zero or one insects (N=132) were correctly scored as 'clean' in ninety-two percent of the cases, with the remainder (eight percent) incorrectly identifying such grain as infested. Samples with two or three insects ('infested' grain) were correctly assessed about sixty-four percent of the time (N=164) with the remainder of the cases begin incorrectly scored as 'clean'. When trials in which two or three insects were used and the distance between placed insects was less than 1.75 sensor units are not considered, the accuracy of the assessment of infested grain increased to about seventy-two percent. As pointed out above, the principal reason that such samples were incorrectly assessed resulted from the failure of test insects to produce sounds above threshold levels.

EXAMPLE 2

This example of the ALFID system uses a cross-correlation method for the analyzing step. An evaluation of this method was accomplished by using a four sensor 0.25 Kg grain container and a self-contained laboratory data acquisition system (the Nicolet System 500). The system simultaneously sampled each of the four sensor outputs at a 250 kHz sampling rate when initiated by its own input signal dependent trigger generation capability. The pre-trigger duration was set to 2 msec (500 samples) to insure capture of the beginning of acoustic signals. The data was then transferred to a spreadsheet program for which a time-domain cross-correlation macro routine had been written. The minimum possible time-shift or resolution of the resulting cross-correlogram was one sample period or 4 usec. Based on an estimated maximum possible time interval of 200 usec for the sensor spacing of 1⅞ inches, the number of time-shifts was limited to 59 (236 usec) in each direction. Because of the uncertainty of the optimum acoustic signal segment size, segments of both 3 msec (750 samples) and 4 msec (1000 samples) were tried (a typical insect sound lasts 8 msec). A total of 35 sounds were collected using eight different infested kernel placements (three to five sounds/placement). An analysis algorithm greatly located the point of origin of 75% of received sounds with an average time interval range of plus or minus 22 usec. This algorithm involved (1) using 3 msec acoustic signal segments, (2) having a minimum acceptable amplitude for cross-correlogram peaks, (3) using a decision making hierarchy for multiple cross-correlogram peaks (from a single sound) that selected the peak with the smallest time-shift unless another peak had an amplitude that was more than 1.7 times as large, and (4) linking together of multiple cross-correlogram peaks (from a single sound) to help avoid identification of a single insect as two or more during peak data summarization. Based on measured time interval consistency for particular infested kernel placements, an ALFID spatial resolution of ¼ of a sensor spacing interval is possible.

It would also be suitable to use a PC type computer (386

CPU minimally) and a plug-in sixteen channel A/D board. A 1 MHz sequential sampling board (Strawberry Tree's Flash-12 Model 1) can provide a 62.5 kHz sampling rate per channel, a 1 usec sampling time offset error between adjacent channels, and a cross-correlogram resolution of 16 usec. The per channel sampling rate needs only be greater than twice the highest frequency in the acoustic signal spectrum. For a 1–10 kHz insect sound bandwidth, a less expensive 320 kHz board would suffice. The sampling time offset error would then be about 3 usec and the cross-correlogram resolution (the per channel sampling period) would be 50 usec. While this cross-correlogram resolution would degrade the ALFID performance, it can be improved by simulating a higher per sampling rate through creation of intermediate 'samples' between acquired samples by interpolation. The trigger signal for the A/D board needs to be externally generated by hardware, since the board does not feature internal triggering. It does have a single analog trigger input with a software selectable triggering level and pre-trigger mode capability. With a trigger signal generator circuit whose output is equal to the highest level on any of the sixteen acoustic signal lines at any given moment, the presence of an acoustic signal on any of the sixteen lines will initiate the acquisition of a block of data containing samples from all sixteen lines. To insure that a single acoustic signal does not initiate collection of multiple blocks of data, a timer on the A/D board can be used to disable the acquisition response to trigger inputs for 7 msec after any received valid trigger. This performs a function identical to the delay release feature accomplished by the "stopwatch" circuit in the amplitude threshold detection embodiment of ALFID. The A/D board software driver can be designed to download sound data from the buffer to computer memory after the acquisition of each sound. The raw sound data in computer memory can be analyzed by performing cross-correlations off-line after the end of the data collection period or even on-line during quiet periods between sounds. The latter possibility would allow for a curtailed data collection period once the system revealed the presence of some minimum number of insects since time is an important factor in grain inspection facilities.

APPENDIX A

```
/*****************************************************
*                                                     *
*                                                     *
*      ALFID18- A program to service the              *
*         ALFID Digital Interface Board               *
*                                                     *
*   The Interface Board supports three 8254 counters  *
*       and two 8255 Input/Output ports               *
*       It receives signals from the                  *
*       ALFID Analog Interface Board                  *
*                                                     *
*   This program supports counter 2 only, so it does  *
*   not count times longer than 11.1454 msec.         *
*                                                     *
*   However,                                          *
*   ALFISR, the original program, supports counters 1 *
*   and 2. It counts times up to 730 sec.             *
*                                                     *
*   This program differs from all previous versions   *
*   in that it does not send any input to the screen, *
*   and no data is input to a disk file until the <Esc> *
*   key is pressed. ALFID18 creates separate files for *
*   the original data: (*.raw), sas data (*.sas),     *
*   ordered summary (*.ord), and sorted summary (*.sum).*
*   It stamps each event with its time of occurrence. *
*                                                     *
*****************************************************/ include <conio.h>
include <dos.h>
#include <graph.h>
#include <math.h>
#include <malloc.h>
#include <stdio.h>
#include <io.h>
#include <stdlib.h>
#include <string.h>
include <time.h> define   IRQ3        0x0b           /* Vector for hardware interrupt #3   */

/*#define IRQ5        0x05*/         /* Debug interrupt, uses the printscreen*/
                                     /* key                                */ define   PORT20DAT   0x20           /* (EOI - 0x20)  to clear the IN Service*/
                                     /* Register                           */
#define   CLEARMASK   0xf7           /* Clear the Mask Register to enable  */
                                     /* interrupts                         */
#define   SETMASK     0x08           /* Set the Mask Register to disable   */
                                     /* interrupts                         */
#define   PORT502CLR  0xe0           /* Output to clear PC4, which clears the*/
                                     /* Analog Interface Board             */
#define   PORT502SET  0xf0           /* Output to undo the PC4 clear       */
#define   READBACK2   0xc8           /* Latch and readback control word for */
                                     /* counter 2                          */
#define   STATUS      0x40           /* Mask to determine if counter has been*/
                                     /* loaded                             */
define   MODE0CNT2   0xb0           /* Control word for mode 0 on Counter 2 */ define   HIFULLCOUNT 0xff           /* Bytes to load full count into high  */
```

```
#define    LOFULLCOUNT     0xfe          /* and low bytes of Counter 2            */
#define    CLOCKSEG        0x0040        /* Segment where BIOS time variable is   */
                                         /* accessed                              */
#define    CLOCKOFFS       0x006c        /* Offset of BIOS time variable          */
                                         /* Macro to make far pointer from a      */
                                         /* segment and offset                    */
#define    TICK            18.20648193
#define    MK_FP(seg,ofs)  ((void far *) \
                           (((unsigned long)(seg) << 16) | (unsigned)(ofs)))
#define    tGet()          (*_tTickCount)   /* Macro for obtaining system         */
                                            /* time                               */
#define    MAXSTORAGE      4096
#define    MAXHITS         64
define    MAXSUMMARY      MAXHITS * 16 * 17 + 1 long _far  *_tTickCount = MK_FP(CLOCKSEG, CLOCKOFFS),  /* Address to store */
                                                        /* system time     */
           *tickcounts;       /* Array to store system time for each event */ unsigned int *count2array,    /* Inputs for Counter2 clock ticks           */
       _far  *sumdat,         /* Array for summary data                    */
             port500 = 0x500, /* Base address of interface board and       */
                              /* Address of PA1                            */
             port501 = 0x501, /* Address of PB1                            */
             port502 = 0x502, /* Address of PC1                            */
             port504 = 0x504, /* Address of PA2                            */
             port505 = 0x505, /* Address of PB2                            */
             port50a = 0x50a, /* Address of Counter 2                      */
             port50b = 0x50b, /* Address of control word for counters      */
             port20  = 0x20,  /* Port 20 receives End of Interrupt         */
             port21  = 0x21;  /* Port 21 accesses Controller Mask Register */ int        port21dat,      /* Original Mask for Controller Mask Register   */
           port21mask,     /* Mask as modified by this program             */
           port502dat,     /* Input to determine if ALFID amplifier        */
                           /* board has cleared (PC1)                      */
           *pa1array,      /* Inputs from PA ports on CN1 and CN2          */
           *pa2array,
           *pb1array,      /* Inputs from PB ports on CN1 and CN2          */
           *pb2array,
           intflag = 0,    /* Flag to indicate the interrupt has been      */
                           /* triggered                                    */
           portptr = 0,    /* Pointer to items stored in port              */
                           /* information array                            */
           col1 = 11,      /* Color settings                               */
           col2 = 14;

double     intsec;         /* time interval in msec                        */ char       buffer[162],    /* Buffers for text output                      */
           titlebuffer[160],
           runno[15],
           *runnop;

FILE       *foutput;       /* Handle to output file                        */ void OrderArray(int, int, unsigned int, unsigned int *);
void WriteOrder(char *, unsigned int *);
```

```c
void (_interrupt _far *oldfuncIRQ3) (void);    /* Vector to ISR now at IRQ3    */
/*void interrupt far *oldfuncIRQ5;*/  /* Vector to any function now at   */
                                      /* IRQ5                             */

/*----------------------------------------------------*/
        /* tStart--Wait for a new tick and return the tick number */
        /* to caller. Makes sure that user starts at the      */
        /* beginning of the tick.                             */
        /*----------------------------------------------------*/ long tStart(void)
    {
    long StartTime,
         temp;

temp = tGet();
    while(temp == (StartTime=tGet()));
    return(StartTime);
    }

/*----------------------------------------------------*/
        /* tDiff--Compute the difference between two time points */
        /* (in sec).                                          */
        /*----------------------------------------------------*/ double tDiff(long StartTime, long EndTime)
    {
    return((double) (EndTime - StartTime) / TICK);
    }

/*----------------------------------------------*/
        /*  ReadISR - interrupt to read counters        */
        /*----------------------------------------------*/ void _interrupt _far ReadISR(void)
    {
    unsigned int   lsbcount2,
                   msbcount2;

port21mask= port21mask | SETMASK;      /* Disable IRQ3 temporarily      */
    outp(port21, port21mask);              /* by setting bit 3 (|00001000)  */
                                           /* of the Interrupt Mask         */
                                           /* Register                      */
    intflag++;                             /* Set flag to indicate that     */
                                           /* routine has been entered.     */
    outp(port50b,READBACK2);               /* Set counter control word      */
                                           /* to read back status of        */
                                           /* counter2, and                 */
    if(inp(port50a) & STATUS)              /* Determine if counter2 has     */
        {                                  /* been loaded (Bit 6=0)         */
        lsbcount2 = HIFULLCOUNT;           /* If not, counter has not       */
        msbcount2 = HIFULLCOUNT;           /* been loaded. Enter the        */
        }                                  /* 2's complement of 0 (FFFF)    */
    else                                   /* as the count                  */
        {
        port502dat = inp(port502) & 0x04;
        if (port502dat == 4)
            {
```

```
            lsbcount2 = 0;            /* Counter has overrun.      */
            msbcount2 = 0;            /* Set count to 0            */
            }
        else
            {
            lsbcount2= inp(port50a);  /* read lsb and msb of       */
            msbcount2 = inp(port50a); /* counter.                  */
            }
        }
    *(count2array + portptr) = (msbcount2 << 8) + (lsbcount2 & HIFULLCOUNT);
    *(palarray+portptr)=inp(port500);  /* Read Port information    */
    *(pblarray+portptr)=inp(port501);
    *(pa2array+portptr)=inp(port504);
    *(pb2array+portptr)=inp(port505);
    *(tickcounts + portptr) = tGet(); /* Get real time of event    */
                                      /* in terms of clock ticks   */
    outp(port50b, MODEOCNT2);         /* Set up Counter 2          */
    outp(port50a, LOFULLCOUNT);       /*     LSB of Counter 2      */
    outp(port50a, HIFULLCOUNT);       /*     MSB of Counter 2      */
    portptr++;                        /* Increment pointer to buffer */
    outp(port502,PORT502CLR);         /* Clear PC4 to clear latches on */
                                      /* analog input board.       */
    outp(port502,PORT502SET);         /* Reset PC4                 */ port21mask= port21mask & CLEARMASK; /* Reenable IRQ3 by clearing bit */
    outp(port21,port21mask);            /* 3 ( & 11110111) of the   */
                                        /* Interrupt Mask Register  */ outp(port20,PORT20DAT);           /* Send the End of Interrupt */
                                      /* (EOI) signal to port 20   */
    }

/*--------------------------------------------*/
            /* InitializeBoard --Subroutine to set up     */
            /* Alfid board for operation                  */
            /*--------------------------------------------*/ int  InitializeBoard(void)
    {
    int    clearflag = 1; /* Flag indicating whether amplifier board */
                          /* has cleared                              */
    long   StartTime;     /* Control to ensure that amplifier board   */
                          /* clear has not hung up system             */
    double timediff;

port21dat=inp(port21);            /* Save original mask         */
    oldfuncIRQ3 = _dos_getvect(IRQ3); /* Save old ISR               */
    _dos_setvect(IRQ3, ReadISR);
    port21mask= port21dat | SETMASK;  /* Disable IRQ3 temporarily   */
    outp(port21, port21dat);          /* by setting bit 3 (|00001000) */

/*********************************************
             *                                           *
             * Set up control words for CN1 and CN2      *
             *   Ports A and B are input for both CN1    *
             *   and CN2. Port C is input in CN2.        *
             *   In CN1, Port C lower is input, upper is *
             *   output. The outputs PC4-PC7 are set     *
             *   high. Accordingly,                      *
             *   Word at 03 is (10010011) = 93           *
```

```
 *      Word at 07 is (10011011) - 9b            *
 *      Word at 02 is (11110000) - F0            *
 *                                               *
 *************************************************/ outp(port500+0x03,0x93);            /*    CN1    */
    outp(port500+0x07,0x9b);            /*    CN2    */

/************************************************
 *                                              *
 * Now, set up counter                          *
 * control words using Port 0x0b :              *
 *      Set up Counter 2                        *
 *      |   Load LSB then MSB                   *
 *      |   |   Use Mode 4                      *
 *      |   |   |   Count in binary             *
 *      _|  _|  _|_  |                          *
 *      (10 11 100 0) - B8                      *
 *                                              *
 *                                              *
 * Next load LSB then MSB of Counter 2          *
 * (Basaddress + A)   FF FF                     *
 *                                              *
 *                                              *
 ***********************************************/ outp(port50b, MODEOCNT2);           /* Set up Counter 2      */
    outp(port50a,LOFULLCOUNT);          /*    LSB of Counter 2   */
    outp(port50a,HIFULLCOUNT);          /*    MSB of Counter 2   */ outp(port502,PORT502SET);           /* Set ALFID amplifier   */
    clearflag = 1;                      /* board, and then       */
    StartTime = tStart();
    while(clearflag == 1 && (timediff = tDiff(StartTime, tGet())) < 1.)
    {
        outp(port502,PORT502CLR);       /* clear PC4 to clear latches */
        port502dat = inp(port502) & 0x02;  /* on amplifier board and  */
        if(port502dat == 2)             /* check whether clear was    */
            clearflag = 0;              /* performed (PC1 set to 1)   */
    }                                   /* If not, send another clear */
    if(timediff >= 1.)
    {
        printf("\nERROR--Amplifier board did not initialize.\n"
               "Please check system and restart.\n");
        return(1);
    }
    outp(port502,PORT502SET);           /* Set PC4 to remove the clear */
    port21dat= port21dat & CLEARMASK;   /* Set the interrupt mask      */
    outp(port21,port21dat);             /* register by clearing bit 3  */
                                        /* ( & 11110111)               */
    return (0);
}

/********************************************************************/
/*MakeNewFile--Make a new accessory file based on original name */
/********************************************************************/ int MakeNewFile(char newfilep, FILE newfileh, char *listfilep,
        char *ext, char *filetype)
```

```c
{
*newfilep = (char *)malloc(strlen(listfilep) + 5);
if(*newfilep == NULL)
        {
        fcloseall();
        printf("\nCannot assign RAM for %f.", listfilep);
        return(1);
        }
strcpy(*newfilep, listfilep);
*newfilep = strtok(*newfilep, ".");
strcat(*newfilep, ext);
*newfileh = fopen(*newfilep, filetype);
if(*newfileh == NULL)
        {
        fcloseall();
        printf("\nCannot open file:  %s", *newfilep);
        return(1);
        }
return (0);
}

/*---------------------------------------------------------*/
        /*  StrLenCheck-- A function that checks to see if a string*/
        /*  is too long for its buffer                             */
        /*---------------------------------------------------------*/ int  StrLenCheck(int errno, char *buf, int length)
{
        if(strlen(buf) > length)
                printf("\nError #%d, Character string length exceeds maximum."
                       "  Abnormal exit\n");
}

/*---------------------------------------------------------*/
        /* InitializeScreen --Subroutine to begin        */
        /* program and get information for data          */
        /*  storage file                                 */
        /*---------------------------------------------------------*/ void InitializeScreen(char *filename, double *testdurationp)
    {
    int     ch,                       /* Storage for keyboard input      */
            fileflag = 1;             /* Flag to indicate whether file   */
                                      /* name is in use                  */ char    timeofdaybuf[25],         /* Buffer to store time of day     */
            idbuf[82],                /* Buffer to hold identification label */
            *bufp,
            testdurbuf[25],
            *buft;

_clearscreen(_GCLEARSCREEN);
    _settextcolor(13);
    sprintf(buffer,"                    ALFID INSECT DETECTION SYSTEM\n");
    _outtext(buffer);
    _settextcolor(12);
    while (fileflag)
            {
            sprintf(buffer, "\nEnter a file label for storage of data files:  ");
            _outtext(buffer);
```

```
            buffer[0] = 20;
            bufp = cgets(buffer);
                if(buffer[1])
                    strcpy(filename, bufp);
            strcat(filename, ".raw");
            if((foutput=fopen(filename,"r")) != NULL)
                {
                    fclose(foutput);
                    _settextcolor(2);
                    sprintf(buffer, "\nFile exists.  Overwrite? (y, n):  ");
                    _outtext(buffer);
                    if((ch = getch()) == 0x79 || ch == 0x59)
                        fileflag = 0;
                }
            else
                fileflag = 0;
            _settextcolor(12);
            }
    sprintf(buffer, "\nEnter an identification label: ");
    _outtext(buffer);
    idbuf[0] = 80;
    bufp = cgets(idbuf);
    _outtext(bufp);
    sprintf(buffer, "\nEnter a run number:  ");
    _outtext(buffer);
    runno[0] = 10;
    runnop = cgets(runno);
    _outtext(runnop);
    sprintf(buffer, "\nEnter number of seconds to run test:  ");
    _outtext(buffer);
    testdurbuf[0] = 20;
    buft = cgets(testdurbuf);
    *testdurationp = strtod(buft, 0);
    strcpy(titlebuffer, "  ; TIME = ");
    _strtime(timeofdaybuf);
    strcat(titlebuffer, timeofdaybuf);
    strcat(titlebuffer, "  ; DATE = ");
    _strdate(timeofdaybuf);
    strcat(titlebuffer, timeofdaybuf);
    strcat(titlebuffer, "\nID = ");
    strcat(titlebuffer, bufp);
    strcat(titlebuffer, "\n");
    if(StrLenCheck(1, titlebuffer, 160))
        exit(1);
    sprintf(buffer, "\nPress any key to begin.");
    _outtext(buffer);
    getch();
    }

/*----------------------------------------------------------*/
            /* PortInfo -- Function that translates bits input from a   */
            /* data port into a portion of the character string sent    */
            /* to the screen buffer                                     */
            /*----------------------------------------------------------*/ unsigned int   PortInfo(int *paarray, int ptr)
    {
    unsigned  int word;

word =  ~(*(paarray+ptr)) & HIFULLCOUNT;
```

```
           if (!word) strcat(buffer,"1 1 1 1 1 1 1 1 ");
    else   if (word == 1)   strcat(buffer,"0 1 1 1 1 1 1 1 ");
    else   if (word == 2)   strcat(buffer,"1 0 1 1 1 1 1 1 ");
    else   if (word == 4)   strcat(buffer,"1 1 0 1 1 1 1 1 ");
    else   if (word == 8)   strcat(buffer,"1 1 1 0 1 1 1 1 ");
    else   if (word == 16)  strcat(buffer,"1 1 1 1 0 1 1 1 ");
    else   if (word == 32)  strcat(buffer,"1 1 1 1 1 0 1 1 ");
    else   if (word == 64)  strcat(buffer,"1 1 1 1 1 1 0 1 ");
    else   if (word == 128) strcat(buffer,"1 1 1 1 1 1 1 0 ");
    else                    strcat(buffer," INVALID DATA  ");
    return (word);
    } unsigned int PortSum(unsigned int portword)
    {
    unsigned int word;

if (!portword) word = 16;
    else  if (portword == 1)   word = 8;  /* strcat(buffer,"0 1 1 1 1 1 1 1 ");*/
    else  if (portword == 2)   word = 9;  /* strcat(buffer,"1 0 1 1 1 1 1 1 ");*/
    else  if (portword == 4)   word = 10; /* strcat(buffer,"1 1 0 1 1 1 1 1 ");*/
    else  if (portword == 8)   word = 11; /* strcat(buffer,"1 1 1 0 1 1 1 1 ");*/
    else  if (portword == 16)  word = 12; /* strcat(buffer,"1 1 1 1 0 1 1 1 ");*/
    else  if (portword == 32)  word = 13; /* strcat(buffer,"1 1 1 1 1 0 1 1 ");*/
    else  if (portword == 64)  word = 14; /* strcat(buffer,"1 1 1 1 1 1 0 1 ");*/
    else  if (portword == 128) word = 15; /*strcat(buffer,"1 1 1 1 1 1 1 0 ");*/
    else  if (portword == 256) word = 0;
    else  if (portword == 512) word = 1;
    else  if (portword == 1024) word = 2;
    else  if (portword == 2048) word = 3;
    else  if (portword == 4096) word = 4;
    else  if (portword == 8192) word = 5;
    else  if (portword == 16384) word = 6;
    else  if (portword == 32768) word = 7;
    else
      {
      printf("Invalid portword=%u\n", portword);
      word=17;
      }
    return (word);
    }
        /*----------------------------------------------------------*/
        /* ScreenOutput--A subroutine that converts input from      */
        /* data arrays into a character string sent to a screen     */
        /* buffer                                                   */
        /*----------------------------------------------------------*/ void StringOutput(char *filename, int portptr, long firsttick)
    {
    char    headbuffer[243],    /* Buffer to hold screen header   */
            elapsedtimebuf[25], /* Buffer to store elapsed time   */
            *sasfilename;

unsigned int cticks,        /* # of ticks on Counter 2        */
            sumptr2,
            sumptr1,
            sumptr,             /* pointers to sumdat array       */
            portword1,          /* words to indicate which ports  */
            portword2,          /* are active                     */
            ptr1,
```

```
                ptr2;
int     ptr = 0;

double  offset;             /* Time offset from start of test    */

FILE    *foutput2;

strcpy(buffer, "FILE - ");
strcat(buffer, filename);
if(MakeNewFile(&filename, &foutput, filename, ".raw", "wt"))
    exit(1);
fwrite (buffer, sizeof(char), strlen(buffer), foutput);
if(MakeNewFile(&sasfilename, &foutput2, filename, ".sas", "wt"))
    exit(1);
fwrite (titlebuffer, sizeof(char), strlen(titlebuffer), foutput);
strcpy(headbuffer,"\n            Port              Interval     Time      Pulse\n
strcat(headbuffer, "      A            B            (msec)      Offset    Number\
strcat(headbuffer, "0 1 2 3 4 5 6 7 0 1 2 3 4 5 6 7              (sec)\n");
_settextcolor(col1);
while (ptr < portptr)
    {
    fwrite (headbuffer, sizeof(char),strlen(headbuffer),foutput);
    strcpy(buffer, "\0");
    portword1 = PortInfo(palarray, ptr) << 8;
    portword1 += PortInfo(pblarray, ptr);
    strcat(buffer,"\n");
    portword2 = PortInfo(pa2array, ptr) << 8;
    portword2 += PortInfo(pb2array, ptr);

/************************************
                 * If invalid data, set ptr to      *
                 * MAXSUMMARY. Else set it to       *
                 * beginning of array that will     *
                 * hold the time differences        *
                 * for each pair of events.         *
                 * The time differences will be     *
                 * sorted and put into a summary.   *
                 ************************************/ if(((ptr1 = PortSum(portword1)) == 17) || ((ptr2 =
            PortSum(portword2)) == 17))
        sumptr = MAXSUMMARY - 1;
    else
        sumptr = (ptr2 * MAXHITS * 16) + (ptr1 * MAXHITS);
    sumdat[sumptr]++;
/*****************************************************************
*                                                                *
* Conversion of counter2 ticks to elapsed time in seconds:       *
*         (# of ticks on counter2)/5.88E6/sec)                   *
*              [Changed from 6.0E6/sec after                     *
*                   calibration]                                 *
*                                                                *
*              -1.70068    E-7 sec                               *
*                                                                *
*****************************************************************/ cticks=count2array[ptr];
    if(sumdat[sumptr] < MAXHITS)
        sumptr1 = sumdat[sumptr];
```

```c
            else
                sumptr1 = MAXHITS - 1;
        sumptr2 = sumptr + sumptr1;
        if (sumptr2 > MAXSUMMARY - 2)
            {
            printf("Sumdat array size exceeded.  Invalid data.");
            sumptr2 = MAXSUMMARY - 2;
            }
        sumdat[sumptr2] = cticks;
        intsec= (double) cticks * 1.70068E-4;
        if(cticks == 0xffff)
            strcpy(elapsedtimebuf, " Count overrun ");
        else
            {
            gcvt(intsec, 10, elapsedtimebuf);
            strcat(buffer, "      ");
            }
        strcat(buffer, elapsedtimebuf);
        offset = tDiff(firsttick, *(tickcounts+ptr));
        gcvt(offset, 7, elapsedtimebuf);
        strcat(buffer, "  ");
        strcat(buffer, elapsedtimebuf);
        sprintf(elapsedtimebuf, "     %i", ptr+1);
        if(StrLenCheck(2, elapsedtimebuf, 25))
            exit(1);
        strcat(buffer, elapsedtimebuf);
        strcat(buffer,"\n");
        if(StrLenCheck(3, buffer, 162))
            exit(1);
        fwrite (buffer, sizeof(char), strlen(buffer), foutput);
        if(cticks == 0xffff)
            strcpy(elapsedtimebuf, "     .      ");
        else
            gcvt(intsec, 10, elapsedtimebuf);
        sprintf(buffer, "%s %i %i %s %7.21f\n", runnop, ptr1, ptr2,
            elapsedtimebuf, offset);
        fwrite(buffer, sizeof(char), strlen(buffer), foutput2);
        ptr++;
        }
    fclose(foutput);
    sprintf(buffer, "Original data saved in: %s\n", filename);
    _outtext(buffer);
    fclose(foutput2);
    sprintf(buffer, "SAS data saved in: %s\n", sasfilename);
    _outtext(buffer);
    }

/*-------------------------------------------------------------*/
        /* SortedSummary--A subroutine that sorts hits collected       */
        /* from ALFID board and prints into a separate *.sum           */
        /* file.                                                       */
        /*-------------------------------------------------------------*/ void SortedSummary(char *filename, unsigned int *order)
    {
    unsigned int tempsort;

char buffer[82],
        *sumfilename;
```

```c
FILE *foutput;                  /* Handle to output file           */ int     hits1,                  /* Pointers for sorting data array */
        hits2,
        hitsort1,
        hitsort2,
        sumptr,
        sumptr1;

if(MakeNewFile(&sumfilename, &foutput, filename, ".sum", "wt"))
        exit(1);
strcpy(buffer, "FILE - ");
strcat(buffer, sumfilename);
fwrite(buffer, sizeof(char), strlen(buffer), foutput);
fwrite (titlebuffer, sizeof(char), strlen(titlebuffer), foutput);
if(sumdat[MAXSUMMARY - 1] > 0)
        {
        sprintf(buffer,"\n%u invalid data point(s).\n",
                sumdat[MAXSUMMARY - 1]);
        fwrite(buffer, sizeof(char), strlen(buffer), foutput);
        }
for (hits1 = 0; hits1 < 16; hits1++)
        {
        for (hits2 = 0; hits2 < 17; hits2++)
                {
                sumptr = hits2 * MAXHITS * 16 + hits1 * MAXHITS;
                if (sumdat[sumptr] > 0)
                        {
                        if (hits2 == 16)
                                {
                                if (sumdat[sumptr] == 1)
                                        sprintf(buffer, "\n%u overrun on Sensor #%i\n",
                                                sumdat[sumptr], hits1);
                                else
                                        sprintf(buffer, "\n%u overruns on Sensor #%i\n",
                                                sumdat[sumptr], hits1);
                                fwrite (buffer, sizeof(char), strlen(buffer),
                                        foutput);
                                }
                        else
                                {
                                if(sumdat[sumptr] == 1)
                                        sprintf(buffer, "\n %u hit at (#%i;#%i).\n"
                                                " intervals (msec):\n",
                                                sumdat[sumptr], hits1, hits2);
                                else
                                        sprintf(buffer, "\n %u hits at (#%i;#%i).\n"
                                                " intervals (msec):\n",
                                                sumdat[sumptr], hits1, hits2);
                                fwrite (buffer, sizeof(char), strlen(buffer),
                                        foutput);
                                if (sumdat[sumptr] < MAXHITS)
                                        sumptr1 = sumdat[sumptr];
                                else
                                        sumptr1 = MAXHITS - 1;
                                for (hitsort1 = 1; hitsort1 < sumptr1; hitsort1++)
                                        {
                                        for (hitsort2 = hitsort1 + 1; hitsort2 <
                                                sumptr1+1; hitsort2++)
                                                {
```

```
                                    if (sumdat[sumptr+hitsort2] <
                                            sumdat[sumptr+hitsort1])
                                        {
                                        tempsort = sumdat[sumptr+hitsort2];
                                        sumdat[sumptr+hitsort2] =
                                            sumdat[sumptr+hitsort1];
                                        sumdat[sumptr+hitsort1] = tempsort;
                                        }
                                    }
                                for (hitsort1 = 1; hitsort1 < sumptr1 + 1;
                                        hitsort1++)
                                    {
                                    intsec= (double) sumdat[sumptr+hitsort1]
                                        * 1.70068E-4;
                                    gcvt(intsec, 10, buffer);
                                    strcat(buffer, "\n");
                                    fwrite (buffer, sizeof(char), strlen(buffer),
                                            foutput);
                                    }
                                }

/* creates an ordered array; inserted by S.Kruss */

OrderArray(hits1, hits2, sumdat[sumptr], order);
                                }
                        }
                    }
        fclose(foutput);
        sprintf(buffer, "Summary saved in: %s\n", sumfilename);
        _outtext(buffer);
        }

/*-------------------------------------------------------*/
            /* Lvector--A subroutine that allocates space for a long */
            /* integer array                                         */
            /*                                                       */
            /*-------------------------------------------------------*/ long *Lvector(int asize)
    {
    long *v;

v = (long *)malloc(asize * sizeof(long));
    if(!v)
        {
        printf("Allocation failure error in function Lvector.");
        exit(1);
        }
    return v;
    }

/*-------------------------------------------------------*/
            /* Ivector--A subroutine that allocates space for an     */
            /* integer array                                         */
            /*                                                       */
            /*-------------------------------------------------------*/ int *Ivector(int asize)
    {
```

```c
    int *v;

v = (int *)malloc(asize * sizeof(int));
    if(!v)
        {
        printf("Allocation failure error in function Ivector.");
        exit(1);
        }
    return v;
    }

/*---------------------------------------------------------*/
        /* Uvector--A subroutine that allocates space for an       */
        /* unsigned integer array                                  */
        /*                                                         */
        /*---------------------------------------------------------*/ unsigned int *Uvector(int asize)
    {
    unsigned int *v;

v = (unsigned int *)malloc(asize * sizeof(int));
    if(!v)
        {
        printf("Allocation failure error in function Uvector.");
        exit(1);
        }
    return v;
    }

/*---------------------------------------------*/
        /*CheckForEsc--A subroutine to check           */
        /*whether user has pressed escape key          */
        /*---------------------------------------------*/ int CheckForEsc(void)
    {
    int answer;
    if(kbhit())
        {
        answer = getch();
        if(answer == 0x1b)
            return(1);
        }
    return(0);
    }

/*---------------------------------------------------------*/
        /* Subroutine that builds a data set for output to         */
        /* Quattro                                                 */
        /*---------------------------------------------------------*/ void OrderArray (int firsthit, int secondhit, unsigned int data,
        unsigned int *order)
    {
    int j = 0;

order[0] = 999; order[47] = 999;
    if (abs(firsthit - secondhit) == 1 || secondhit == 16)
        {
```

```
            if ((firsthit - secondhit) == 1)
                j = 0;
            if (((firsthit - secondhit) == -1) && secondhit != 16)
                j = 2;
            if (secondhit == 16)
                j = 1;

/* Array "order" looks like: 00(empty),01,02,10,11,12,20,21,22...*/ order[3 * firsthit + j] = data;
        }
    } /* END OF ORDERARRAY */

/*---------------------------------------------------*/
            /* Subroutine that outputs Quattro data set to a file.*/
            /*---------------------------------------------------*/ void WriteOrder(char *filename, unsigned int *orderfile)
    {
    int  i;

char *ordfilename;

if(MakeNewFile(ªilename, &foutput, filename, ".ord", "wt"))
            exit(1);
    for (i = 1; i < 47; i ++)
            fprintf(foutput,"%u\n", *(orderfile+i));
    fclose(foutput);
    sprintf(buffer, "Spreadsheet summary saved in: %s\n", ordfilename);
    _outtext(buffer);

} /* END OF WRITEORDER */

/*---------------------------------------------------*/
            /*            Main section of program            */
            /*---------------------------------------------------*/ void main(void)
    {
    char filename[25] = "ALFID.FIL";  /* Buffers to hold file names    */ unsigned int   zero = 0,
                   zindex,
            _far   *order;

long           firsttick,       /* Tick count at start of test   */
                   endtest;

double         testduration;    /* Number of sec to run test     */ palarray  = Ivector(MAXSTORAGE);  /* Arrays to store Port and    */
    pa2array  = Ivector(MAXSTORAGE);  /* Counter information         */
    pblarray  = Ivector(MAXSTORAGE);
    pb2array  = Ivector(MAXSTORAGE);
    count2array = Uvector(MAXSTORAGE);
    sumdat    = Uvector(MAXSUMMARY);
    order     = Uvector(48);
    tickcounts = Lvector(MAXSTORAGE);
                                      /* Initialize summary data and */
                                      /* output file arrays          */
```

```
        for (zindex = 0; zindex < MAXSUMMARY; zindex++)
            sumdat[zindex] = 0;
        for (zindex = 0; zindex < 48; zindex++)
            order[zindex] = 0;

/*      oldfuncIRQ5=_dos_getvect(IRQ5);   */ /* old interrupt calls       */
/*      _dos_setvect(IRQ5,(ExitAlfISR)); */ /* saved for debugging        *
/*      _dos_setvect(IRQ5,(ReadISR));    */

InitializeScreen(filename, &testduration);
        if(InitializeBoard() == 0)
            {
            _settextcolor(7);
            sprintf(buffer, "\nData collection is now in progress.\n"
                "Press <Esc> to exit.\n");
            _outtext(buffer);
            firsttick = tStart();
            endtest = (long) (testduration * TICK) + firsttick;

/* Wait for interrupts until buffer full, or user     */
                    /* escapes, or test duration is exceeded              */ while(portptr < MAXSTORAGE)
                {
                port21mask= port21mask | SETMASK;
                outp(port21, port21mask);
                if((CheckForEsc() != 0) || (tGet() - endtest > 0))
                    break;
                port21mask= port21mask & CLEARMASK;  /* Reenable IRQ3 by clearing bit */
                outp(port21,port21mask);             /* 3 ( & 11110111) of the        */
                                                     /* Interrupt Mask Register       */
                }
                    /* Test is over                */
                    /* Disable IRQ3 temporarily    */
                    /* by setting bit 3 (|00001000)*/
                    /* and save data files         */ port21mask= port21mask | SETMASK;
            outp(port21, port21mask);
            sprintf(buffer,"\nBreak at event #%d, test duration = %7.21f sec\n", portptr, tDiff
                (firsttick, tGet()));
            _outtext(buffer);
            StringOutput(filename, portptr, firsttick);   /* Output data to files*/
            SortedSummary(filename, order);
            WriteOrder(filename, order);
            }
        _dos_setvect(IRQ3,(oldfuncIRQ3));   /* Set the IRQ3 vector back to its*/
                                            /* position at start of program   */
        outp(port21,port21dat);             /* and reset the original mask.   */
        _settextcolor(7);

/*      _dos_setvect(IRQ5,(oldfuncIRQ5)); */
        }  /* END OF MAIN */
```

We claim:

1. An acoustic location fixing insect detector for detecting adult or larval insects in agricultural commodities comprising:

(a) a container for holding agricultural commodities;

(b) a plurality of acoustic sensors attached to said container for detecting sound waves emanating from insects in said agricultural commodities and converting said sound waves to electrical signals;

(c) an amplifier means connected to each of said plurality of acoustic sensors for amplifying said electrical signals;

(d) an analyzer means connected to each of said amplifier means for receiving the resulting amplified electrical signals and determining which of said plurality of acoustic sensors detects a sound emanating from an insect first, a first detection, determining which of said plurality of acoustic sensors detects said sound second, a second detection, and determining the time interval between said first detection and said second detection; and forming a determination;

(e) an indicating means connected to said analyzer means for using the determination made by said analyzer means to determine a locus of possible points defining a plane which contains the detected insects, to count a total number of different planes and to equate the number of different planes to a number of different insects.

2. The acoustic location fixing insect detector of claim 1 further comprising a filter means connected between said amplifier means and said analyzer means for filtering out sound wave frequencies caused by unwanted noise.

3. The acoustic location fixing insect detector of claim 1 further comprising a soundproof box of a size sufficient to hold said container inside.

4. The acoustic location fixing insect detector of claim 1 wherein the agricultural commodities includes grains, fruits, nuts, vegetables or legumes.

5. The acoustic location fixing insect detector of claim 1 wherein said acoustic sensors are piezoelectric acoustic sensors.

6. The acoustic location fixing insect detector of claim 1 wherein said acoustic sensors have high sensitivity and flatness of response to frequencies of 1.5 to 5.5 KHz.

7. The acoustic location fixing insect detector of claim 1 further comprising an amplitude threshold detecting means connected between said amplifier means and a logic means for detecting only the electrical signals having amplitudes above a predetermined level.

8. The acoustic location fixing insect detector of claim 1 wherein said analyzer means is a stopwatch circuit which comprises:

(a) a plurality of first place latches and second place latches each of said plurality of latches being connected to each of said amplifier means through a threshold detecting means;

(b) each of said plurality of second place latches being connected to a first place latch in order to prevent corresponding first place and second place latches from being reset;

(c) a gating logic means connected to said plurality of first and second place latches for enabling and disabling said first and second place latches in a sequence to determine which sensor detects a sound emanating from an insect first, a first detection, and by which sensor detects sound emanating from said insect second, a second detection; and (d) a timing means connected to said first and second place latches for determining the time interval between said first detection and said second detection.

9. The acoustic location fixing insect detector of claim 8 wherein said gating logic means comprises:

(a) means for initializing all latches;

(b) means for identifying which of the first place latches receives an electrical signal from the first detection;

(c) means for disabling the second place latch connected to the first place latch identified in (b);

(d) means for disabling all first place latches;

(e) means for enabling all other second place latches;

(f) means for starting the timing means;

(g) means for identifying which of the second place latches receives an electrical signal from the second detection; and (h) means for stopping said timing means.

10. A method of acoustical location fixing of adult or larval insects in agricultural commodities comprising the steps of:

(a) acoustically detecting sound waves emanating from insects in an agricultural commodity sample with a plurality of acoustical sensors and converting said sound waves to electrical signals;

(b) determining which of said plurality of acoustic sensors is first to detect sound waves emanating from an insect, a first detection, and which of said plurality of acoustic sensors is second to detect sound waves emanating from said insect, a second detection;

(c) determining the difference in time between said first detection and said second detection;

(d) analyzing the determinations from step (b) and step (c) to determine a locus of possible points defining a plane which contains the detected insect;

(e) repeating steps (a) through (d) for each sound produced in said agricultural commodity sample;

(f) counting the total number of different planes determined by steps (a) through (e) and;

(g) equating the number of planes to the number of different insects.

11. A method of acoustical location fixing of adult or larval insects in agricultural commodities as described in claim 10 wherein steps (b), (c), (d), and (f) are accomplished by a computer.

12. A method of acoustical location fixing of adult or larval insects in agricultural commodities as described in claim 10 wherein steps (a) through (f) are repeated a minimum number of times to reduce the probability of false positives due to noise.

13. The method of claim 10 wherein the agricultural commodities include grains, fruits, legumes, nuts, or vegetables.

14. A method of acoustical location fixing of adult or larval insects in agricultural commodities as described in claim 10 wherein the electrical signals are amplified, bandpass filtered to filter out unwanted noise and amplitude threshold detected to select amplitudes only above a predetermined level and establish when said amplitudes are first above said predetermined level on individual channels.

15. A method of acoustical location fixing of adult or larval insects in agricultural commodities as described in claim 10 wherein the determination of the first and second detections comprises the steps of:

(a) initializing a plurality of first place latches; each of said first place latches being connected to one of said plurality of acoustical sensors and to one of a plurality of second place latches;

(b) identifying which of said first place latches receives the first detection;

(c) disabling said one of a plurality of second place latches connected to the first place latch described in step (b), disabling all first place latches, enabling all other second place latches, and beginning a time interval timer;

(d) identifying which of said plurality of second place latches receives the second detection;

(e) disabling said plurality of second place latches; and (f) stopping the time interval timer.

16. A method of acoustical location fixing of adult or larval insects in agricultural commodities comprising the steps of:

(a) acoustically detecting sound waves emanating from insects in an agricultural commodity sample and converting said sound waves to electrical signals with a plurality of piezoelectric transducers;

(b) amplifying said electrical signals;

(c) bandpass filtering the amplified electrical signals to filter out unwanted noise;

(d) determining which of said plurality of piezoelectric transducers is first to detect sound waves emanating from an insect, a first detection, and which of said plurality of piezoelectric transducers is second to detect sound waves emanating from same said insect, a second detection, by:

($d_a$) initializing a plurality of first place latches, each of said first place latches being connected to one piezoelectric transducer of said plurality of piezoelectric transducers and to one of a plurality of second place latches;

($d_b$) identifying which of said first place latches receives the first detection;

($d_c$) disabling said one of said plurality of second place latches connected to the first place latch described in ($d_b$), disabling all first place latches, enabling all other second place latches, and beginning a time interval timer;

($d_d$) identifying which of said plurality of second place latches receives the second detection;

($d_e$) disabling all of said plurality of second place latches; and ($d_f$) stopping the time interval timer;

(e) determining the time interval between the first detection and the second detection;

(f) analyzing the determinations made in steps (d) and (e) to determine a locus of possible points defining a plane which contains the insect;

(g) repeating steps (a) through (f) for each sound produced in said agricultural commodity sample; and (h) counting a total number of planes detected by steps (a) through (g);

(i) equating the total number of planes to a number of different insects.

17. A method of acoustical location fixing of adult or larval insects in agricultural commodities comprising the steps of:

(a) acoustically detecting sound waves emanating from insects in an agricultural commodity sample with a plurality of acoustical sensors and converting said detected sound waves from each sensor to electrical signals;

(b) analyzing each of said electrical signals by cross-correlation to determine which of said plurality of acoustic sensors is first to detect sound waves emanating from an insect, a first detection, which of said sensors is second to detect sound waves emanating from said insect, a second detection, and the time difference between said first and second detection;

(c) analyzing the determinations from step (b) to determine a locus of possible points defining a plane which contains the detected insect;

(d) repeating steps (a), (b), and (c) for each sound produced in said agricultural commodity sample; and (e) counting a total number of different planes and equating the number of different planes to a number of different insects.

* * * * *